US006248359B1

(12) United States Patent
Faour

(10) Patent No.: US 6,248,359 B1
(45) Date of Patent: Jun. 19, 2001

(54) MULTI-TABLET OXYBUTYNIN SYSTEM FOR TREATING INCONTINENCE

(75) Inventor: Joaquina Faour, Buenos Aires (AR)

(73) Assignee: Laboratorios Phoenix U.S.A., Inc., Buenos Aires (AR)

( * ) Notice: Subject to any disclaimer, the term of this patent is extended or adjusted under 35 U.S.C. 154(b) by 0 days.

(21) Appl. No.: 09/477,968

(22) Filed: Jan. 5, 2000

(51) Int. Cl.[7] ............... A61K 9/26; A61K 9/14; A61K 9/22; A61K 9/24; A61K 9/28

(52) U.S. Cl. ............ 424/469; 424/468; 424/470; 424/472; 424/473; 424/474; 424/475; 424/476; 424/479; 424/480; 424/482; 424/484; 424/486; 424/488; 514/534

(58) Field of Search .................. 424/457, 450, 424/459, 460, 461, 462, 468, 469, 470, 471, 472, 474, 489, 490, 491, 492, 493, 494, 495, 496, 497, 498; 514/4, 534

(56) References Cited

U.S. PATENT DOCUMENTS

| | | | |
|---|---|---|---|
| 5,368,861 | 11/1994 | Ushimaru et al. | 424/451 |
| 5,399,359 | 3/1995 | Baichwal | 424/464 |
| 5,532,278 | 7/1996 | Aberg et al. | 514/617 |
| 5,612,351 | 3/1997 | Mulhauser et al. | 514/304 |
| 5,654,005 | 8/1997 | Chen et al. | 424/480 |
| 5,674,895 | 10/1997 | Guittard et al. | 514/534 |
| 5,712,271 | 1/1998 | Mulhauser et al. | 514/212 |
| 5,736,577 | 4/1998 | Aberg et al. | 514/617 |
| 5,788,987 | 8/1998 | Busetti et al. | 424/480 |
| 5,840,754 | * 11/1998 | Guittard et al. | 514/534 |
| 5,912,268 | 6/1999 | Guittard et al. | 514/534 |
| 6,004,582 | * 12/1999 | Faour et al. | 424/473 |

FOREIGN PATENT DOCUMENTS

| | | |
|---|---|---|
| 04163901 | 12/1993 | (JP) . |
| 06009388 | 1/1994 | (JP) . |
| WO 96/12477 | 10/1994 | (WO) . |

OTHER PUBLICATIONS

Douchamps et al.; The Pharmacokinetics of Oxybutynin in Man; Eur. J. Clin. Pharmacol. (1988) 35:515–520.

Lukkari et al.; Effect of Food on the Bioavailability of Oxybutynin from a Controlled Release Tablet; Eur. J. Clin. Pharmacol. (1996) 50:221–223.

Birns et al; Controlled–Release Oxybutynin Maintains Efficacy with a 43% Reduction in Side Effects Compared with Conventional Oxybutynin Treatment; Ann. Mtg. of Inter. Cont. Soc. (1997)16(5), 429–430.

Nilsson et al.; Comparison of a 10 mg Controlled Release Oxybutynin Tablet with a 5 mg Oxybutynin Tablet in Urge Incontinent Patients; Neurology and Urodynamics (1997) 16: 533–542.

Hughes, et al.; Measurement of oxybutynin and its N–desethyl metabolite in plasma, and its Application to pharmacokinetic studies in young, elderly, and frail elderly volunteers.;Xenobiotica (1992) 7:859–869.

Sirkia, et al.; Use of hydrophilic polymers to control drug release from press–coated oxybutynin hydrochloride tablets.; S.T.P. Pharma Sci, (1993) 6:453–458.

Appell, et al.; Clinical evaluation of a Sustained Release Form of Oxybutynin (Ditropan SR) for the Treatment of Detrusor Hyperreflexia in Neuropathic Patients; Urodynamics Soc. Symp. Abstracts (1990) 228.

Nilsson et al., "Comparison of a 10–mg Controlled Release Oxybutynin Tablet With a 5–mg Oxybutynin Tablet in Urge Incontinent Patients," Neurology and Urodynamics, vol. 16, pp. 533–542, 1997.*

* cited by examiner

*Primary Examiner*—Allen J. Robinson
(74) *Attorney, Agent, or Firm*—Rick Matos; Innovar, L.L.C.

(57) ABSTRACT

The present invention provides a simple multi-tablet system for the treatment of urinary incontinence with oxybutynin. Particular embodiments of the invention provide a first tablet that releases oxybutynin over a short period of time, e.g. less than six hours, and a second tablet that releases oxybutynin over an extended period of time, e.g., eighteen to twenty-four hours, to maintain therapeutically effective levels oxybutynin in the mammal for a period of about twenty four hours. Unlike other systems, this system is easily adaptable to compensate for patient to patient variability in response to oxybutynin therapy. The invention also provides a method of treating urinary incontinence with the above system and a kit comprising various first and second tablets to rapidly develop a patient's preferred dosing regimen, i.e., the dosing regimen which provides the greatest therapeutic benefit and/or least amount or severity of side effects.

31 Claims, 7 Drawing Sheets

MULTI-TABLET OXYBUTYNIN SYSTEM FOR TREATING INCONTINENCE

FIELD OF THE INVENTION

This invention pertains to a multi-tablet system for the treatment of urinary incontinence. More particularly, it pertains to a multi-tablet system wherein oxybutynin is released from two tablets at different times to provide a combined sustained delivery of oxybutynin for about a one day period.

BACKGROUND OF THE INVENTION

Oxybutynin is widely known for the treatment of urinary incontinence. Ditropan™ tablets are commercially available tablets that provide a rapid release of oxybutynin in the stomach and upper intestinal tract. Rapid release tablets are typically administered at a rate of about 3–4 tablets per day to treat urinary incontinence. Rapid release tablets, however, typically have undesirable side-effects associated with them due to the high plasma oxybutynin concentrations they provide. These tablets also have a short duration of action due to the short half-life ($t_{1/2} \approx 2$ hr) of oxybutynin in plasma.

In order to overcome these disadvantages, controlled release tablets of oxybutynin have been developed. In general, known controlled release tablets provide a sustained delivery of oxybutynin for a period of up to 8–30 hours after administration depending upon the formulation used. Sequential administration (2–3 times per day) of oxybutynin tablets having the same release profile is known.

U.S. Pat. No. 5,399,359 to Baichwal, the entire disclose of which is hereby incorporated by reference, discloses many different controlled release tablet formulations which provide a controlled release of oxybutynin for periods of up to 8, 12, 16, 18, 24 or 30 hours.

U.S. Pat. Nos. 5,912,268, 5,840,754 and 5,674,895 to Guittard, the entire disclosures of which are hereby incorporated by reference, disclose osmotic device formulations which deliver oxybutnin at a controlled rate for a period of about 24 hours.

Appell et al. ("Clinical Evaluation of a Sustained Release Form of Oxybutynin, *Urodynamics Society Symposium Abstracts* (1990), pg. 228), the entire disclosure of which is hereby incorporated by reference, discloses a controlled release tablet Ditropan™ SR, which provides a controlled delivery of oxybutynin for about 8–12 hours.

Sirkiä et al. ("Use of hydrophilic polymers to control drug release from press-coated oxybutynin hydrochloride tablets", *S. T. P. Pharmacia Sci.* (1993), 3(6), pg. 453–458), the entire disclosure of which is hereby incorporated by reference, discloses a controlled release tablet formulation which provides a controlled delivery of oxybutynin for about 8–12 hours.

Japanese Patent Applications Serial No. 9,388 and No. 163,901 to Enomoto et al., the entire disclosures of which are hereby incorporated by reference, disclose controlled release tablet formulations which deliver oxybutynin at a controlled rate for a period of about 12 hours for once or twice-a day administration.

Osmotic devices and other tablet formulations are known for their ability to provide controlled release of a wide range of drugs. Such osmotic devices and other tablet formulations are disclosed in U.S. Pat. No. 4,014,334 to Theeuwes et al., U.S. Pat. No. 4,576,604 to Guittard et al., Argentina Patent No. 234,493, U.S. Pat. No. 4,673,405 to Guittard et al., U.S. Pat. No. 5,558,879 to Chen et al., U.S. Pat. No. 4,810,502 to Ayer et al., U.S. Pat. No. 4,801,461 to Hamel et al., U.S. Pat. No. 5,681,584 to Savastano et al., U.S. Pat. No. 3,845,770 and Argentina Patent No. 199,301, the entire disclosures of which are hereby incorporated by reference.

It is well known that eating habits have an effect upon the observed plasma oxybutynin concentration in humans. (Lukkari et al., "Effect of food on the bioavailability of oxybutynin from a controlled release tablet", *Eur. J. Clin. Pharmacol.*, (1996), 50(3), pg. 221–223). Specifically, eating breakfast was shown to reduce the mean retention time of oxybutynin in the plasma. Moreover, patient age and health also have an effect upon the observed plasma oxybutynin concentration in humans (Hughes et al. "Measurement of oxybutynin and its N-desethyl metabolite in plasma, and its application to pharmacokinetic studies in young, elderly and frail elderly patients", *Xenobiotica* (1992), 22(7), pg. 859–869). Specifically, a trend of increasing peak plasma levels and bioavailability was observed with increasing patient age and frailty, with the differences being more apparent between the active elderly and frail elderly groups than between the active elderly and the young volunteers. Currently available controlled release oxybutynin formulations are not able to compensate for the observed patient to patient variability in oxybutynin therapy.

Thus, a need remains for an adaptable system of treating urinary incontinence which provides a controlled delivery of oxybutynin and maintains safe and therapeutically effective levels of oxybutynin in patients while accounting for their age or health. None of the single tablet prior art systems can fulfill this need.

Moreover, while the prior art discloses a wide variety of tablet formulations that individually provided a rapid or controlled release of oxybutynin, none of the art discloses a system for treating urinary incontinence comprising two tablet dosage forms having different release profiles which together provide a sustained delivery of oxybutynin for a period of about one day.

The present system is capable of providing a broader range of overall release profiles for oxybutynin due to the combination of two or more tablets having different release profiles. Further, the present system provides greater control over the delivery of oxybutynin in treating urinary incontinence and is therefore adaptable from patient to patient.

SUMMARY OF THE INVENTION

The present invention provides a two-tablet system for the treatment of urinary incontinence, wherein the tablets together provide a sustained delivery of oxybutynin for about one day or a period of about 18–26 hours, and preferably about 24 hours. In one embodiment, the present system comprises:

a first tablet which releases oxybutynin after at least about one second after administration of the first tablet; and a second tablet which releases oxybutynin after at least about three hours after administration of the second tablet;

wherein the first and second tablets together provide a sustained delivery of oxybutynin for a total period of about 18–26 hours.

In another embodiment, the present system comprises:

a first tablet having a first release profile for the release of oxybutynin; and a second tablet having a different second release profile for the release of oxybutynin, wherein the first and second tablets together provide a sustained delivery of oxybutynin for a period of about 18–30 hours.

According to various preferred embodiments, (a) the first and second tablets are administered concurrently; (b) the first and second tablets are administered sequentially; (c) the first and second tablets maintain a therapeutic level of oxybutynin in the plasma of the mammal for a period of about 24 hours; (d) the first tablet is a rapid release dosage form and the second tablet is a controlled release dosage form; (e) the first tablet releases all of its oxybutynin within about three hours after administration of the first tablet, and the second tablet begins to release its oxybutynin within about five hours after administration of the first tablet and completes its release of oxybutynin within about 24 hours after administration of the first tablet; (1) the first tablet releases all of its oxybutynin less than two hours after administration of the first tablet, and the second tablet begins to release its oxybutynin within about four hours after administration of the first tablet and completes its release of oxybutynin within about 23 hours after administration of the first tablet; (g) the first tablet is a controlled release tablet and the second tablet is a controlled release tablet, the tablets having different release profiles (h) the first tablet maintains therapeutic levels of oxybutynin for a period of up to about 3 hours after administration and the second tablet maintains therapeutic levels of oxybutynin for a period of about 3 hours after administration to about 24 hours after administration; and/or (i) the first tablet maintains therapeutic levels of oxybutynin for a period of up to about 12 hours after administration and the second tablet maintains therapeutic levels of oxybutynin for a period of about 12 hours after administration to about 24 hours after administration.

Another aspect of the invention provides a method of treating urinary incontinence with oxybutynin comprising the steps of:

administering a first tablet having a first release profile for the release of oxybutynin; and administering a second tablet having a different second release profile for the release of oxybutynin, wherein the first and second tablets together provide a sustained delivery of oxybutynin for a period of about 18–30 hours.

According to other preferred embodiments of the invention, (a) the first and second tablets are administered concurrently and the second tablet begins to release its oxybutynin after the first tablet has completed releasing at least a majority of its oxybutynin; (b) the first and second tablets are administered sequentially, the first tablet begins to release its oxybutynin after at least one second after administration of the first tablet, the second tablet is administered at least about two hours after administration of the first tablet and the second tablet begins to release its oxybutynin after at least about two hours after administration of the second tablet; (c) the first tablet releases its oxybutynin in the upper GI tract and the second tablet releases its oxybutynin in the lower GI tract; (d) the first tablet is a gastric release tablet and the second tablet is an enteric and/or colonic release tablet; (e) the first and second tablets are administered sequentially; (f) the first tablet begins its release of oxybutynin about one hour after administration of the first tablet; and/or (g) the second tablet is adminstered at least one hour after administration of the first tablet, and the second tablet begins to release its oxybutynin immediately after administration of the second tablet.

Target therapeutic levels of oxybutynin are in the range of about 1–12 ng, preferably 3–8 ng and more preferably 4–7 ng, of oxybutynin per ml of plasma.

The first and second tablets can deliver their respective charges of oxybutynin in the various regions of the intestinal tract including the buccal cavity, esophagus, stomach, duodenum, jejunum, small intestine, large intestine and rectum.

Other features, advantages and embodiments of the invention will become apparent to those skilled in the art by the following description, accompanying examples and appended claims.

BRIEF DESCRIPTION OF THE FIGURES

The following drawings are part of the present specification and are included to further demonstrate certain aspects of the invention. The invention may be better understood by reference to one or more of these drawings in combination with the detailed description of the specific embodiments presented herein.

Figure 1:
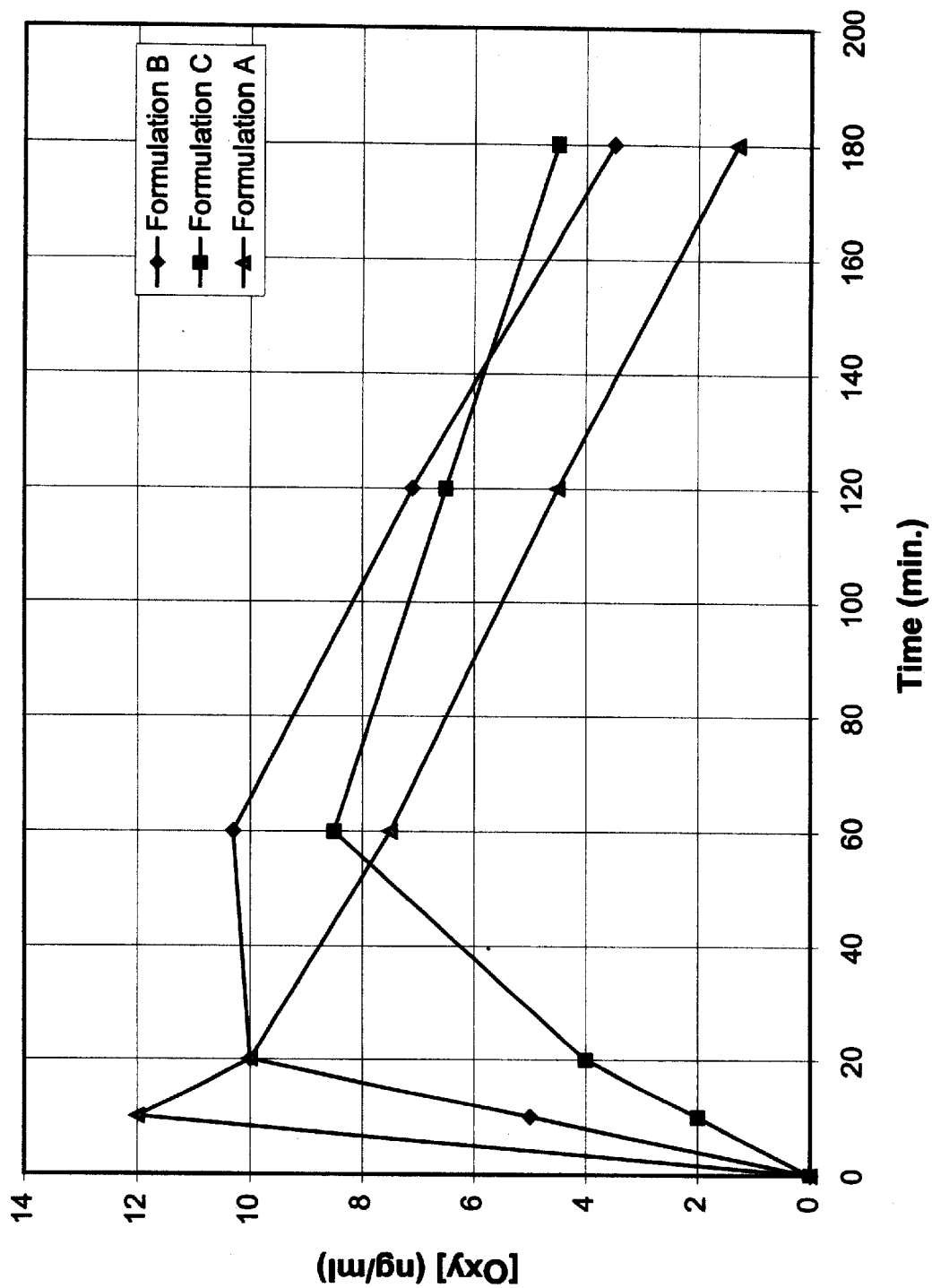
FIG. 1 depicts plasma oxybutynin concentration profiles for various exemplary first tablets according to the invention.

The data that is depicted in FIGS. 1–7 reflects results that would be expected from administration of the respective tablets or systems described herein.

DETAILED DESCRIPTION OF THE INVENTION

Oxybutynin is commercially available as the free base or in its hydrochloride salt form from Abbott Laboratories Pharmaceutical Division (United States of America), Seloc AG (France), Sifa Ltd, (Ireland), Orga rnol SA, Synkem Div. Plasto SA, Cedex (France), Gruppo Lepetit SA, Garessio (Italy) and Juzen Chemical Co. Ltd. The invention provides for the administration of oxybutynin in its free base, racemic, optically pure and/or pharmaceutically acceptable salt forms. The optically pure form of oxybutynin is commercially available from Sepracor (United States of America).

Oxybutynin is available in a rapid release tablet dosage form from Alza (Palo Alto, Calif.), Rosemont (Denver, Co.), Sidmark Laboratories (NJ), Vintage Pharmaceuticals (Huntsville, Ala.), Laboratorios Phoenix (Argentina), and Leiras OY (Finland). Oxybutynin is typically completely released from these tablet dosage forms within about 0.1–3.0 hours after administration.

Oxybutynin is available in controlled release osmotic device tablet dosage forms called Ditropan™ XL from Alza Corporation (Palo Alto, Calif.) and called Ditropan™ UD from Laboratios Phoenix (Argentina) and as a non-osmotic device tablet dosage form called Cystrin™ CR from Leiras OY (Finland). Oxybutynin is released from these tablet dosage forms at a controlled rate over a period of about 24 hours. Controlled release dosage forms of oxybutynin can also be manufactured according to the U.S. and foreign patents and patent applications incorporated herein by reference, and in particular according to U.S. Pat. Nos. 5,399,359, 5,912,268, 5,840,754, and 5,674,895, Japanese Patent Applications Serial No. 9,388 and No. 163,901. Controlled release dosage forms containing oxybutynin can also be prepared according to Nilsson et al. (Neurourol. Urodyn. (1997), 16(6), pg. 533–42), International Publications No. WO 95/23,593, and No. WO 96/12,477 and U.S. Pat. No. 5,368,861, the entire disclosures of which are hereby incorporated by reference. Controlled release dosage forms can also be manufactured according to the examples herein.

The oxybutynin can be formulated as its pharmaceutically acceptable salts. As used herein, "pharmaceutically acceptable salts" refer to derivatives of the disclosed compounds wherein the therapeutic compound is modified by mailing acid or base salts thereof. Examples of pharmaceutically acceptable salts include, but are not limited to, mineral or organic acid salts of oxybutynin. The pharmaceutically acceptable salts include the conventional non-toxic salts, for example, from non-toxic inorganic or organic acids. For example, such conventional non-toxic salts include those derived from inorganic acids such as hydrochloric, hydrobromic, sulfinic, sulfonic, sulfamic, phosphoric, nitric and the like; and the salts prepared from organic acids such as amino acids, acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like. Lists of suitable salts are found in *Remington's Pharmaceutical Sciences*, 17th ed., Mack Publishing Company, Easton, Pa., 1985, p. 1418, the disclosure of which is hereby incorporated by reference.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The tablet dosage forms useful in the present invention include pressed tablets, layered tablets, osmotic device tablets, coated tablets, uncoated tablets, enteric coated tablets, multiple compressed tablets, centered tablets (tablets containing another tablet inside), prolonged release tablets, slow release tablets, buccal and sublingual tablets, and molded tablets.

FIG. 1 depicts exemplary plots of expected plasma oxybutynin concentration (ng of oxybutynin per ml of plasma) versus time (min.) for a mammal having been administered various rapid release dosages forms of oxybutynin. Formulation A is a rapidly dissolving tablet that dissolves in mouth of the mammal within about one to 20 seconds after administration. Such as formulation might include effervescent or other very rapidly dissolving or chewable tablets. Formulation B is a rapidly dissolving tablet formulation that dissolves within about 10 min to one hour after administration. Formulation C is a rapidly dissolving tablet formulation, such as a Ditropan™ tablet, that dissolves within about 30 min to about 3 hours after administration. Each tablet of Formulations A, B, and C contain 1–5, preferably 1–2.5, mg of oxybutynin. As the time period of oxybutynin release increases, the $C_{max}$ of oxybutynin in the plasma decreases and the $T_{max}$ increases.

Figure 2:
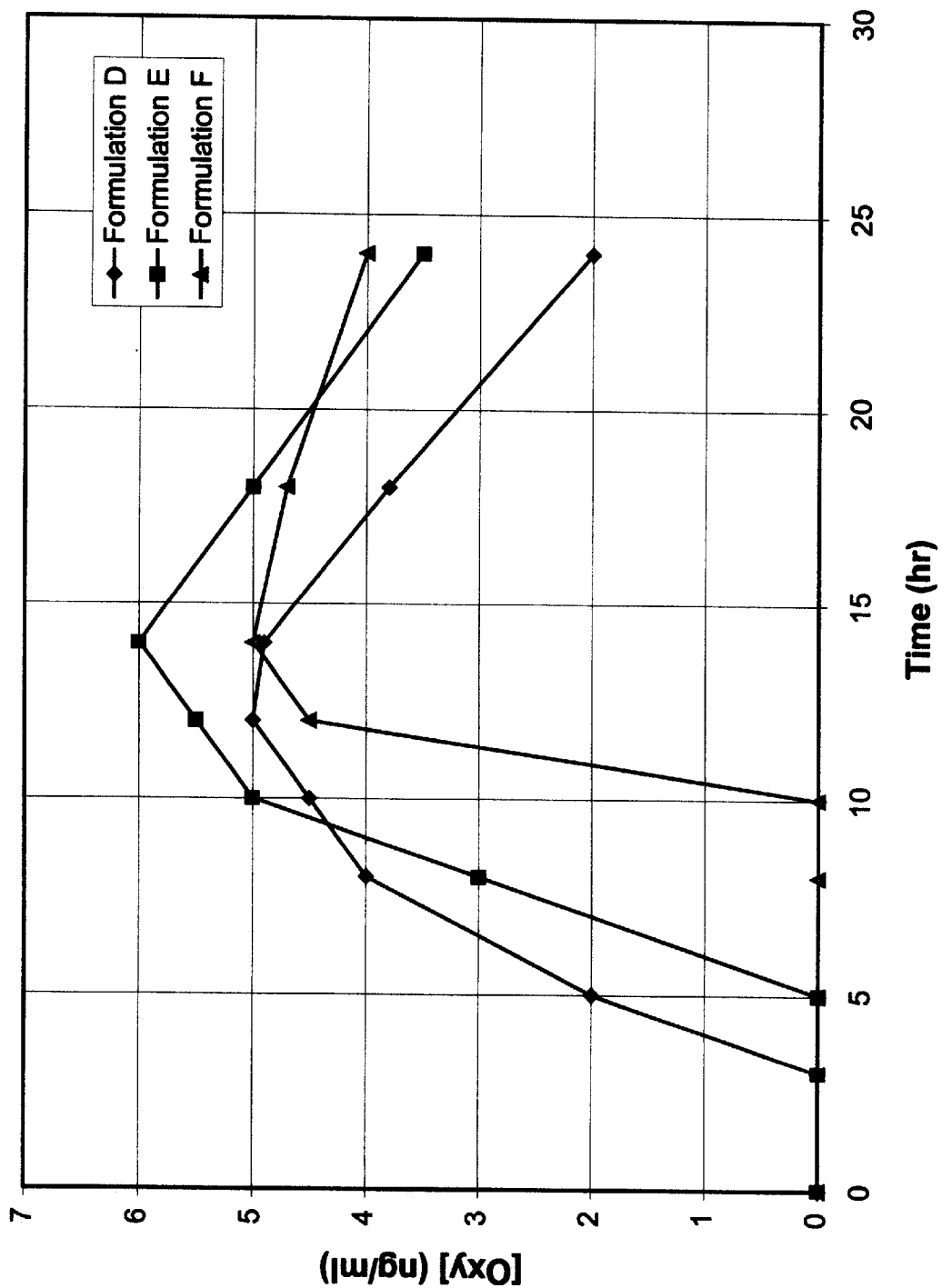
FIG. 2 depicts plasma oxybutynin concentration profiles for various exemplary second tablets according to the invention.

FIG. 2 depicts exemplary plots of expected plasma oxybutynin concentration (ng of oxybutynin per ml of plasma) versus time (min.) for a mammal having been administered various controlled release dosages forms of oxybutynin. Formulation D is a controlled release tablet that begins to release oxybutynin within about three hours after administration and continues to release oxybutynin for another about 20 hours. Formulation E is a controlled release tablet that begins to release oxybutynin within about 5 hours after administration once the tablet has reached the small intestine and continues to release oxybutynin for another about 18 hours. Formulation F is a controlled release tablet that begins to release oxybutynin within about 10 hours after administration once the tablet has reached the large intestine and continues to release oxybutynin for another 10–20 hours. Each tablet of Formulations D, E and F contains 5 mg of oxybutynin. Again, as the time of oxybutynin release increases, the $C_{max}$ of oxybutynin in the plasma decreases and the $T_{max}$ increases.

Figure 3:
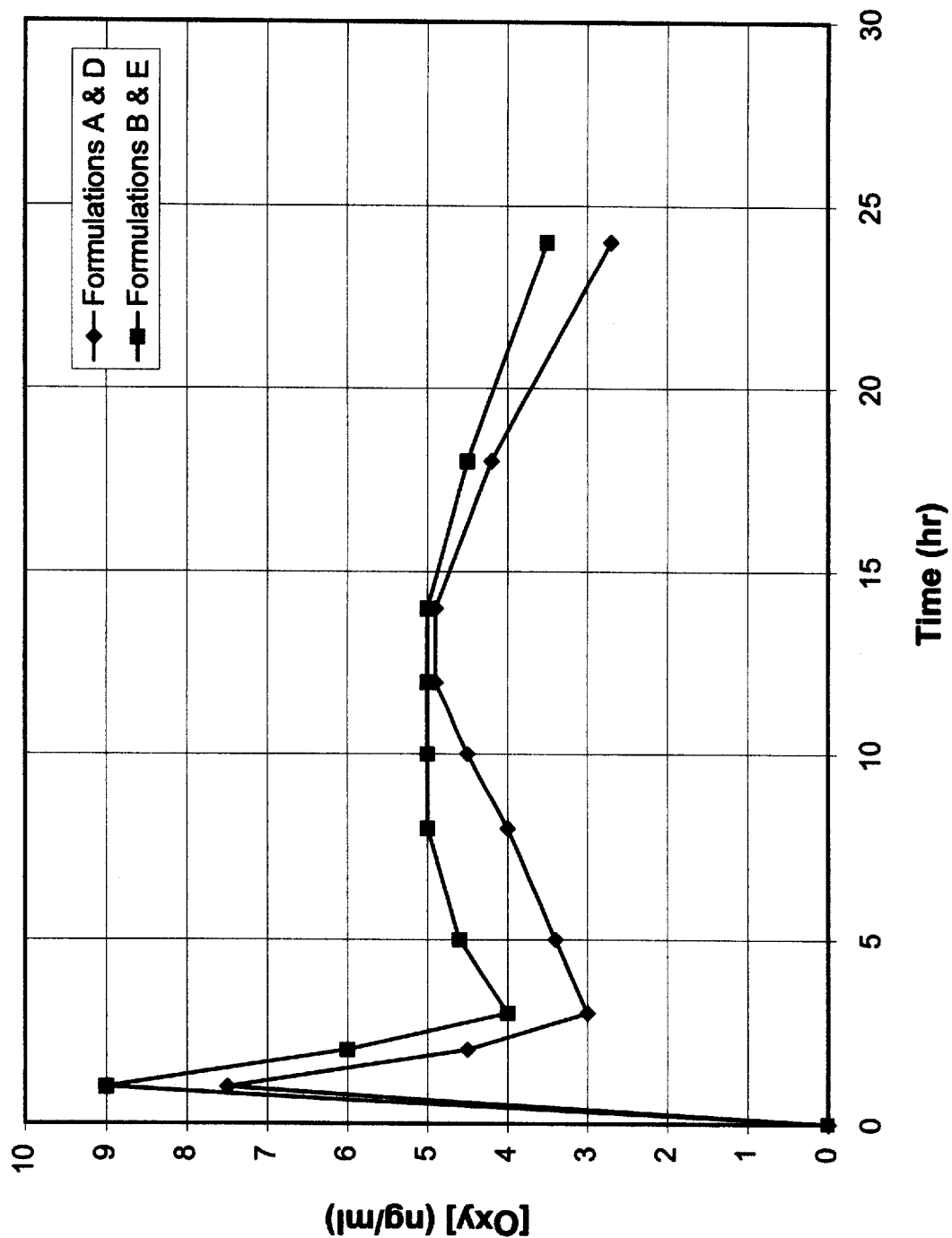
FIG. 3 depicts two exemplary overall plasma oxybutynin concentration profiles for different formulations of the first tablet of FIG. 1 and of the second tablet of FIG. 2 used in combination.

FIG. 3 depicts exemplary plots of expected overall plasma oxybutynin concentration (ng of oxybutynin per ml of plasma) versus time (min.) for a mammal having been concurrently administered: (a) the rapid release tablet Formulation A and the controlled release tablet Formulation D (see line —■—); and (b) the rapid release tablet Formulation B and the controlled release tablet Formulation E (see line —◆—). Note that before the plasma oxybutynin concentration created by the tablet Formulation A drops below about 1 ng/ml, the tablet Formulation D has already begun to release its oxybutynin.

According to a preferred embodiment of the invention, the first tablet is a rapid release tablet containing about 0.01 to about 5 mg, preferably about 1 to about 7 mg, more preferably about 2 mg to about 6 mg, of oxybutynin. The first tablet will preferably provide therapeutic levels of oxybutynin for a period of less than about 6 hours, preferably about 4.0, and more preferably about 3 hours after administration of the first tablet.

According to another preferred embodiment, the second tablet is a controlled release tablet containing about 5 to about 15 mg, preferably about 5 to about 10 mg, and more preferably about 5 to about 8 mg, of oxybutynin. The second tablet will provide therapeutic levels of oxybutynin for a period beginning no sooner than about 3 hours and ending no later than about 24 hours, and preferably beginning no sooner than about 4 hours and ending no later than about 22 hours after administration.

According to yet another preferred embodiment, the first tablet is a controlled release tablet that completely releases its oxybutynin charge within about 8 hours, more preferably about 6 hours, after administration. In this embodiment, the second tablet is a controlled release tablet that begins to release its oxybutynin charge after the first tablet has released at least a majority of its oxybutynin charge. The second tablet completes releasing its oxybutynin charge within about 23–24 hours after administration of the first tablet. In this embodiment, the tablets are administered sequentially if each tablet begins releasing oxybutynin shortly after administration, and the tablets are administered concurrently if the first tablet begins to release oxybutynin shortly after administration and the second tablet has a delayed release of oxybutynin.

Figure 4:
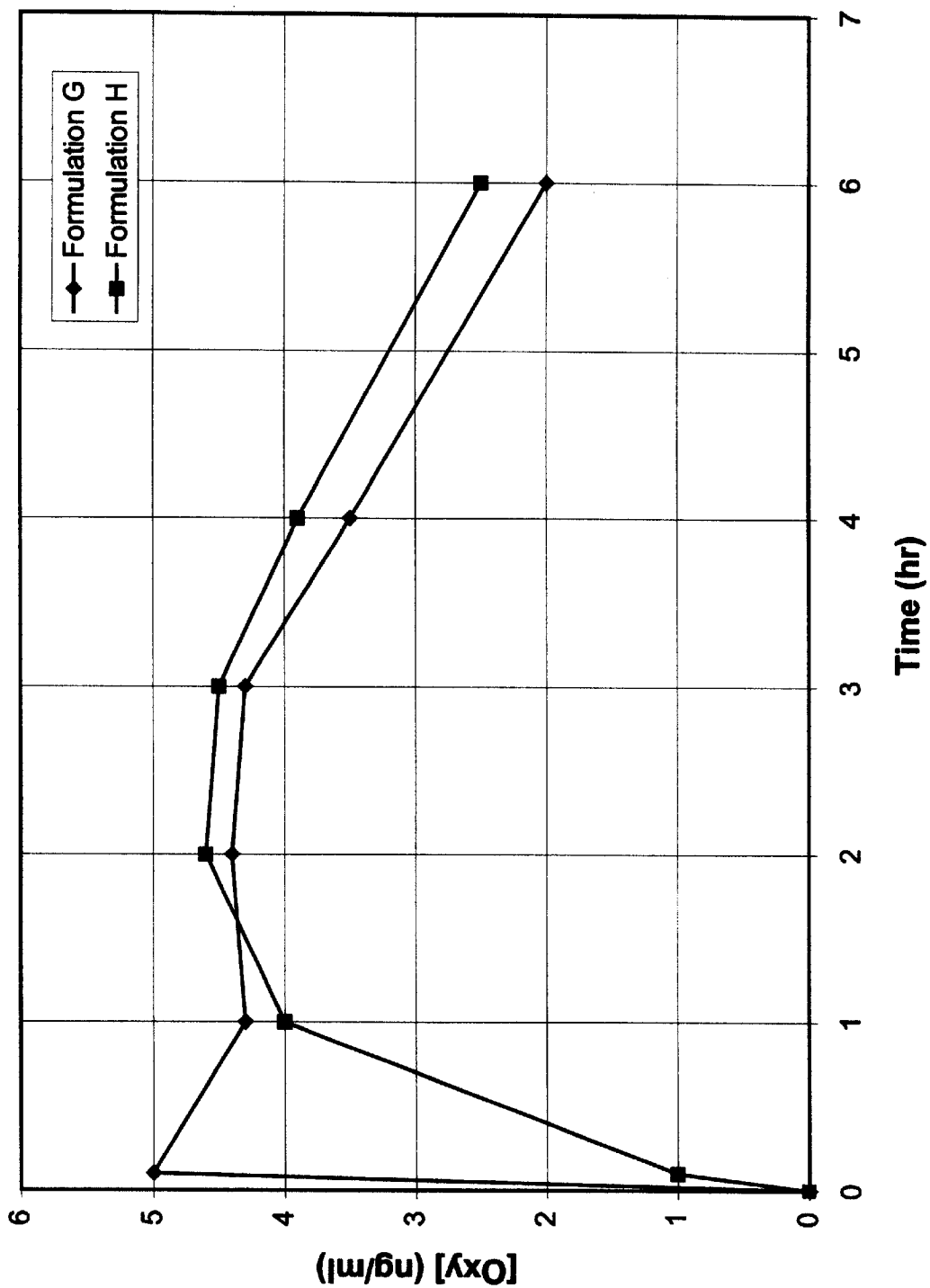
FIG. 4 depicts two exemplary plasma oxybutynin concentration profiles for the short acting controlled release Formulations G and H of the first tablet.

FIG. 4 depicts exemplary plots of expected plasma oxybutynin concentration versus time for two different short acting controlled release tablets. The tablet Formulation G comprises an outer rapid release layer (0.5 mg oxybutynin) and an inner controlled release core (2.0 mg of oxybutynin). The tablet formulation H comprises a controlled release core (2.5 mg of oxybutynin).

Figure 5:
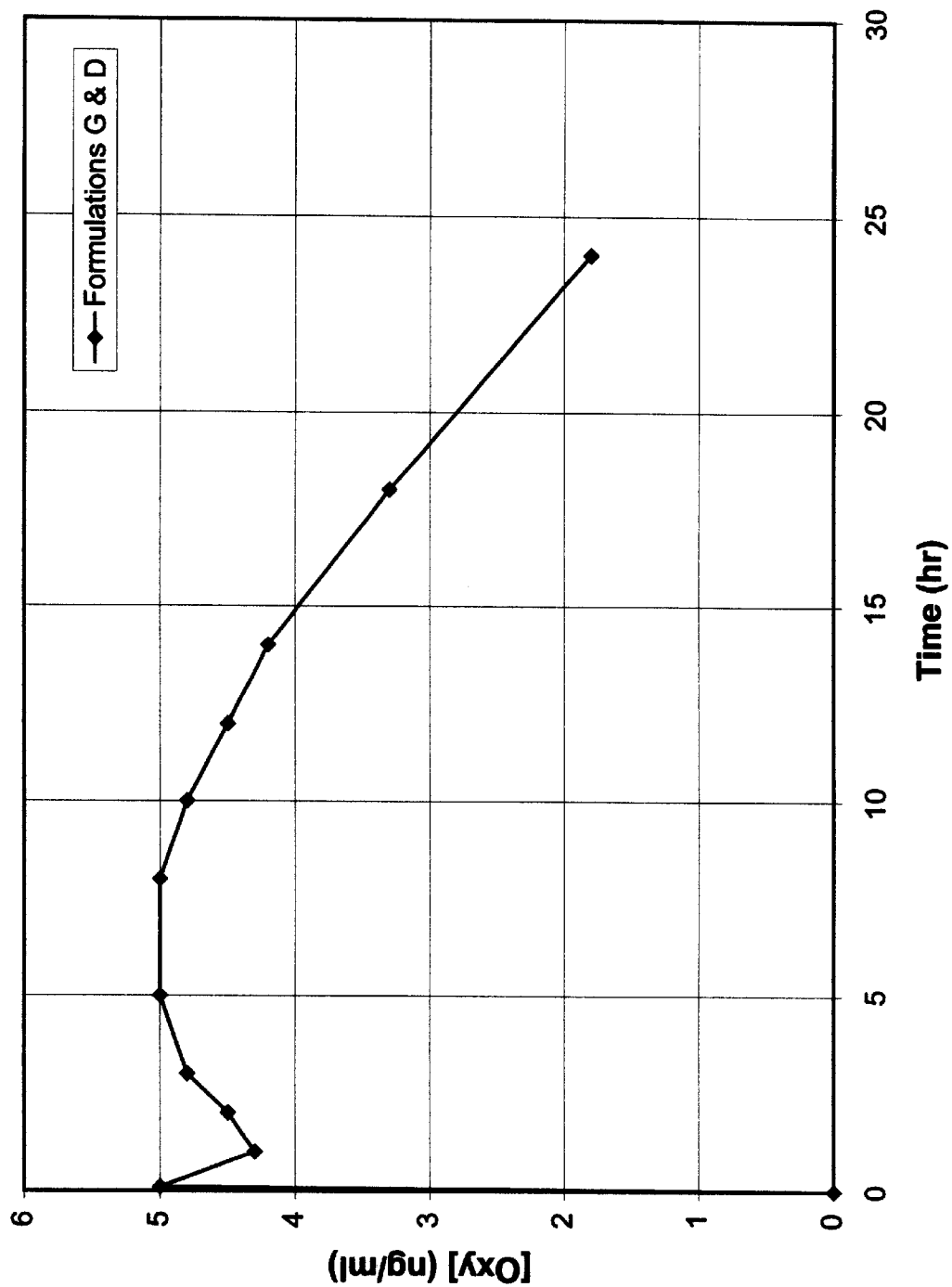
FIG. 5 depicts an overall plasma oxybutynin concentration profile for an exemplary system comprising tablet Formulations G and D.

FIG. 5 depicts an exemplary plot of expected overall plasma oxybutynin concentration (ng of oxybutynin per ml of plasma) versus time (min.) for a mammal having been concurrently administered the short acting controlled release first tablet Formulation G and the long acting controlled release second tablet Formulation D. This system advantageously maintains therapeutic plasma levels of oxybutynin, between about 2 ng/ml to about 6 ng/ml, for about a 24 hour period after administration of the first tablet.

Figure 6:
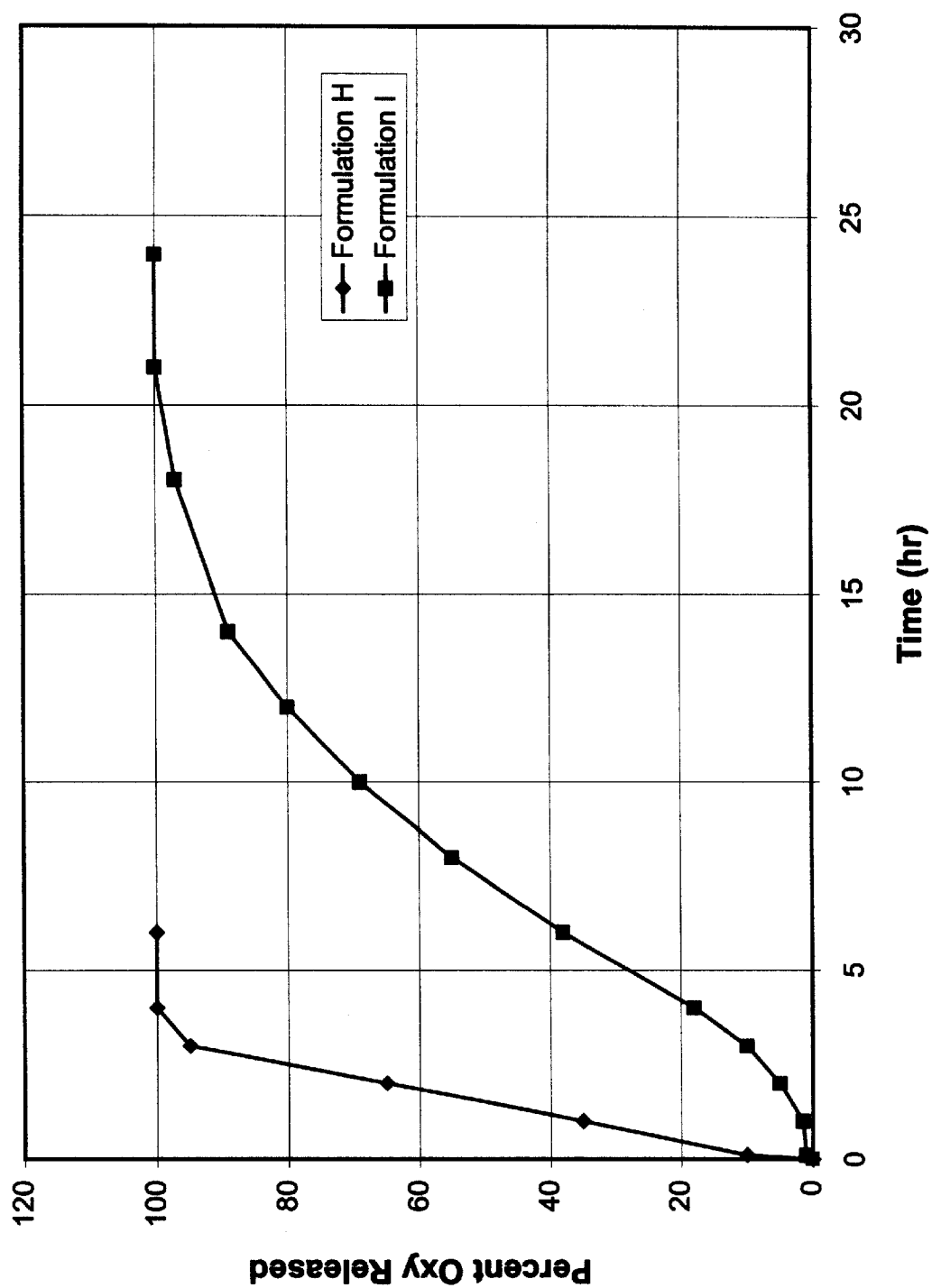
FIG. 6 depicts the release profiles for the tablet Formulations H and I.
Figure 7:
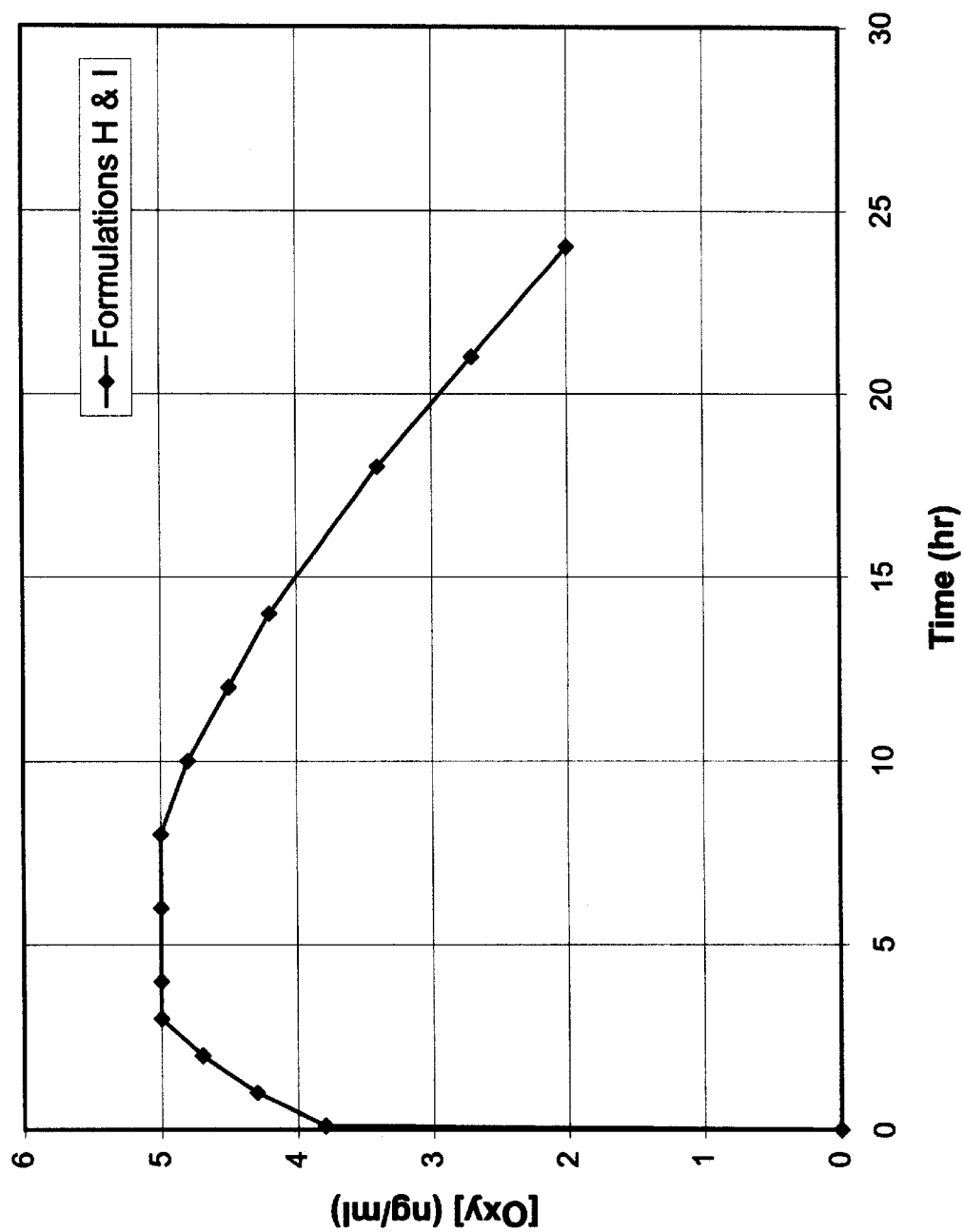
FIG. 7 depicts an overall plasma oxybutynin concentration profile for an exemplary system comprising tablet Formulations H and I.

FIG. 6 depicts two exemplary expected release profiles of oxybutynin the first tablet Formulation H and the second tablet Formulation I. Neither of the tablet Formulations H or I individually maintains therapeutic levels of oxybutynin for a full 24 hour period. The tablets must be administered as a unit dose to maintain therapeutic levels of oxybutynin for a 24 hour period. The tablet Formulation H releases its dose over a period of 4–5 hours, and the tablet Formulation I releases its dose over a period of 20–24 hours.

Depending upon the particular combination of first and second tablets used, the multi-tablet system of the invention will provide an expected overall oxybutynin release profile resembling release profiles of controlled release systems that are pH-dependent or pH-independent; diffusion or dissolution controlled; pseudo-zero order, zero-order, pseudo-first order, first-order or second-order; or slow, delayed, timed or sustained release or otherwise controlled.

All of the tablet formulations of the invention will provide therapeutically effective levels of oxybutynin for at least a predetermined period of time. The first and second tablets of the invention will together provide therapeutically effective amounts of oxybutynin for a period of not less than 18 hours and not more than 30 hours, preferably not less than 20 hours and not more than 28 hours, and more preferably not less than 22 hours and not more than 24 hours. The artisan of ordinary skill will understand that administration of a single unit dose period of time may be insufficient to maintain therapeutic plasma levels of oxybutynin for up to 24–30 hours and that multiple unit doses administered over an equal number of days may be required to maintain therapeutic plasma levels of oxybutynin for up to 24–30 hours.

When the first and second tablets are administered concurrently, they may be administered individually or they may be encased in a capsule, such as a hard or soft gelatin capsule. Alternatively, the first tablet can be a rapidly dissolving tablet that dissolves in the buccal cavity or a chewable tablet, while the second tablet is one that would be swallowed whole. Still, the first tablet could be a short acting controlled release tablet that begins to release oxybutynin shortly after administration while the second tablet is a conventional long acting delayed and controlled release tablet that begins to release oxybutynin at least three hours after administration.

A unit dose of the system according to the invention comprises a first tablet and a second tablet, each tablet having a different release profile. The first and second tablets can be packaged separately or together. Unit doses can also be packaged separately or together. A single unit dose is administered on a daily basis in order to treat urinary incontinence. The tablets of the unit dose, however, may be administered sequentially or concurrently. For example, the first and second tablets may be taken at about the same time, e.g., within 0–60 min. of each other, or at different times, e.g., the second tablet is taken more than 60 min. after the first tablet.

The rapid release tablets and short acting controlled release tablets, which are used as the first tablets of the invention, will provide therapeutically effective levels of oxybutynin generally for a period of less than 8 hours, preferably less than 6 hours. The short acting controlled release tablets, which are used as the second tablets of the invention, will provide therapeutically effective levels of oxybutynin generally for a period of not less than 16 hours and not more than 23 hours, preferably not less than 18 hours and not more than 22 hours.

As noted above, the short acting controlled release tablet Formulation G includes a rapid release external coat containing oxybutynin. The external coat can be applied to the surface of the core of the tablet according to methods of preparing similar tablets which are known to those of ordinary skill. Such methods include, for example, applying to its surface solids in solution or suspension through the use of a sprayer that spreads them uniformly over the core or by employing compression or other suitable methods known to those of ordinary skill in the art. The external coat can comprise poly(vinyl pyrrolidone) (PVP) and poly(ethylene glycol) (PEG) and can further comprise materials such as, by way of example and without limitation, hydroxypropyl methylcellulose (HPMC), ethylcellulose (EC), hydroxyethylcellulose (HEC), sodium carboxymethyl-cellulose (CMC), dimethylaminoethyl methacrylate-methacrylic acid ester copolymer, ethylacrylate-methylmethacrylate copolymer (GA-MMA), C-5 or 60 SH-50 (Shin-Etsu Chemical Corp.) and combinations thereof. The external coat can also comprise dissolution aids, stability modifiers, and bioabsorption enhancers When the external coat comprises a combination of materials, the relative amounts and ratios of those materials can be varied as desired. For example, when the external coat comprises PVP and PEG, the ratio of PVP:PEG will generally range from about 1–65% by weight of PVP: about 0.1–30% by weight of PEG based upon the weight of the external coat.

The oxybutynin present in the external coat is present in an amount ranging from about 0.1 to 99% by weight of the coat. This wide range provides great latitude in the design and application of the first tablet. Those of ordinary skill in the art will appreciate that the particular amount of oxybutynin employed will vary according to, among other things, the desired pharnacokinetic behavior in a mammal. For example, if the initial burst of oxybutynin release is intended to be small, then the external coat would include about 0.01 mg to about 0.5 mg of oxybutynin. If the initial burst of oxybutynin release is intended to be moderate, the external coat would include about 0.5 mg to about 5 mg of oxybutynin.

When a rapidly dissolving coat is used in the tablet formulations of the invention, the coat will generally comprise an inert and non-toxic material which is at least partially, and preferably substantially completely, soluble or erodible in an environment of use. The rapidly dissolving coat will be soluble in the buccal cavity and/or upper GI tract, such as the stomach, duodenum, jejunum or upper small intestines. Exemplary materials are disclosed in U.S. Pat. Nos. 4,576,604 and 4,673,405, and the text Pharmaceutical Dosage Forms: Tablets Volume 1, Second Edition. A.

Lieberman. ed. 1989, Marcel Dekker, Inc. the relevant disclosures of which are hereby incorporated by reference. In preferred embodiments, the rapidly dissolving coat will be soluble in saliva, gastric juices, or acidic fluids.

The long acting controlled release tablet formulations that provide a delayed and sustained release of oxybutynin may include an enteric coat which is soluble or erodible in intestinal juices, substantially pH neutral or basic fluids but for the most part insoluble in gastric juices or acidic fluids. A wide variety of other polymeric materials are known to possess these various solubility properties. Such other polymeric materials include, by way of example and without limitation, cellulose acetate phthalate (CAP), cellulose acetate trimelletate (CAT), poly(vinyl acetate) phthalate (PVAP), hydroxypropylmethylcellulose phthalate (HP), poly(methacrylate ethylacrylate) (1:1) copolymer (MA-EA), poly(methacrylate methylmethacrylate) (1:1) copolymer (MA-MMA), poly(methacrylate methylmethacrylate) (1:2) copolymer, Eudragit L-30-D™ (MA-EA, 1:1), Eudragit™ L-100-55™ (MA-EA, 1:1), hydroxypropylmethylcellulose acetate succinate (HPMCAS), Coateric™ (VAP), Aquaten™ (CAP), AQUACOAT™ (HBPMCAS) and combinations thereof. The enteric coat can also comprise dissolution aids, stability modifiers, and bioabsorption enhancers. When the enteric coat is intended to be dissolved, eroded or become detached from the core in the colon, such as for the tablet of Formulation F, materials such as hydroxypropylcellulose, microcrystalline cellulose (MCC, Avicel™ from FMC Corp.), poly (ethylene-vinyl acetate) (60:40) copolymer (EVAC from Aldrich Chemical Co.), 2-hydroxyethylnethacrylate (HEMA), MMA, terpolymers of HEMA: MMA:MA synthesized in the presence of N,N'-bis(methacryloyloxyethyloxycarbonylamino)-azobenzene, azopolymers, enteric coated timed release system (Time Clock® from Pharmaceutical Profiles, Ltd., UK) and calcium pectinate can be used.

A preferred polymeric material for use in the enteric coat involves enteric materials that resist the action of gastric fluid avoiding permeation through the semipermeable wall while one or more of the materials in the core of the tablet are solubilized in the intestinal tract thereby allowing delivery of the oxybutynin in the core by osmotic pumping in an osmotic device to begin. A material that easily adapts to this kind of requirement is a poly(vinylpyrrolidone)-vinyl acetate copolymer, such as the material supplied by BASF under its Kollidon VA64 trademark, mixed with magnesium stearate and other similar excipients. The enteric coat can also comprise povidone, which is supplied by BASF under its Kollidon K 30 trademark, and hydroxypropyl methylcellulose, which is supplied by Dow under its Methocel E-15 trademark. The materials can be prepared in solutions of having different concentrations of polymer according to the desired solution viscosity. For example, a 10% P/V aqueous solution of Kollidon K 30 has a viscosity of about 5.5–8.5 cps at 20° C., and a 2% P/V aqueous solution of Methocel E-15 has a viscosity of about 13–18 cps at 20° C.

The enteric coat can comprise one or more materials that do not dissolve, disintegrate, or change their structural integrity in the stomach and during the period of time that the tablet resides in the stomach. Representative materials that keep their integrity in the stomach can comprise a member selected from the group consisting of (a) keratin, keratin sandarac-tolu, salol (phenyl salicylate), salol beta-naphthylbenzoate and acetotannin, salol with balsam of Peru, salol with tolu, salol with gum mastic, salol and stearic acid, and salol and shellac; (b) a member selected from the group consisting of formalized protein, formalized gelatin, and formalized cross-linked gelatin and exchange resins; (c) a member selected from the group consisting of myristic acid-hydrogenated castor oil-cholesterol, stearic acid-mutton tallow, stearic acid-balsa mn of tolu, and stearic acid-castor oil; (d) a member selected from the group consisting of shellac, ammoniated shellac, ammoniated shellac-salol, shellac-wool fat, shellac-acetyl alcohol, shellac-stearic acid-balsam of tolu, and shellac n-butyl stearate; (e) a member selected from the group consisting of abietic acid, methyl abictate, benzoin, balsam of tolu, sandarac, mastic with tolu, and mastic with tolu, and mastic with acetyl alcohol; (f) acrylic resins represented by anionic polymers synthesized from methacrylate acid and methacrylic acid methyl ester, copolymeric acrylic resins of methacrylic and methacrylic acid and methacrylic acid alkyl esters, copolymers of alkacrylic acid and alkacrylic acid alkyl esters, acrylic resins such as dimethylaminoethylmethacrylate-butylmethacrylate-methyhnethacrylate copolymer of 150,000 molecular weight, methacrylic acid-methylmethacrylate 50:50 copolymer of 135,000 molecular weight, methacrylic acid-methylmethacrylate-30:70-copolymer of 135,000 mol. wt., methacrylic acid-dimethylaminoethyl-methacrylate-ethylacrylate of 750,000 mol. wt., methacrylic acid-methylmethacrylate-ethylacrylate of 1,000,000 mol. wt., and ethylacrylate-methylmethacrylate-ethylacrylate of 550,000 mol. wt; and, (g) an enteric composition comprising a member selected from the group consisting of cellulose acetyl phthalate, cellulose diacetyl phthalate, cellulose triacetyl phthalate, cellulose acetate phthalate, hydroxypropylmethylcellulose phathalate, sodium cellulose acetate phthalate, cellulose ester phthalate, cellulose ether phthalate, methylcellulose phthalate, cellulose ester-ether phthalate, hydroxypropyl cellulose phthalate, alkali salts of cellulose acetate phthalate, alkaline earth salts of cellulose acetate phthalate, calcium salt of cellulose acetate phthalate, ammonium salt of hydroxypropyl methylcellulose phthalate, cellulose acetate hexahydrophthalate, hydroxypropyl methylcellulose hexahydrophthalate, polyvinyl acetate phthalate diethyl phthalate, dibutyl phthalate, dialkyl phthalate wherein the alkyl comprises from 1 to 7 straight and branched alkyl groups, aryl phthalates, and other materials known to one or ordinary skill in the art.

When the controlled release tablet, such as for exemplary Formulations D, E, and F, is an osmotic device, the semipermeable membrane of the osmotic device is formed of a material that is substantially permeable to the passage of fluid from the environment of use to the core and substantially impermeable to the passage of active agent from the core. Many common materials known by those of ordinary skill in the art are suitable for this purpose. Exemplary materials are cellulose esters, cellulose ethers and cellulose esters-ethers. However, it has been found that a semipermeable membrane consisting essentially of cellulose acetate (CA) and poly(ethylene glycol) (PEG), in particular PEG 400, are preferred when used in combination with the other materials required in the present osmotic device. This particular combination of CA and PEG provides a semipermeable membrane that gives the osmotic device a well controlled release profile for the active agent in the core and that retains its chemical and physical integrity in the environment of use. The ratio of CA:PEG generally ranges from about 50–99% by weight of CA: about 50–1% by weight of PEG, and preferably about 95% by weight of CA: about 5% by weight of PEG. The ratio can be varied to alter permeability and ultimately the release profile of the osmotic device. Other preferred materials can include a selected member of the group of cellulose acylates such as cellulose acetate, cellulose diacetate, cellulose triacetate and combinations thereof. Many suitable polymers, include those disclosed in Argentine Patent No. 199,301 and other references cited herein, the disclosures of which are hereby incorporated by reference.

The core of all the tablet Formulations A-I of the present invention will comprise oxybutynin, at least one pharmaceutically acceptable excipient and optionally one or more other materials. Generally, the first tablet formulations will comprise about 0.1–5.0 mg of oxybutynin and will be present in an amount ranging from 0.1–99.9% by weight of the uncoated tablet core. Generally, the second tablet formulations will comprise about 2.5–25 mg, preferably about 4–20 mg, of oxybutynin and will be present in an amount ranging from 0.1–90% by weight of the uncoated tablet core. Preferred ranges will vary according to the active agent use and the intended use of the osmotic device.

When the controlled release tablet is an osmotic device, osmotically effective solutes, osmotic agents or osmagents are added. These osmagents will aid in either the suspension or dissolution of the oxybutynin in the core. Exemplary osmagents include organic and inorganic compounds such as salts, acids, bases, chelating agents, sodium chloride, lithium chloride, magnesium chloride, magnesium sulfate, lithium sulfate, potassium chloride, sodium sulfite, calcium bicarbonate, sodium sulfate, calcium sulfate, calcium lactate, d-mannitol, urea, tartaric acid, raffinose, sucrose, alpha-d-lactose monohydrate, glucose, combinations thereof and other similar or equivalent materials which are widely known in the art. Osmagents can also be incorporated to the core of the osmotic device to control the release of oxybutynin therefrom.

The tablets of the invention can also comprise adsorbents, antioxidants, buffering agents, colorants, flavorants, sweetening agents, tablet antiadherents, tablet binders, tablet and capsule diluents, tablet direct compression excipients, tablet disintegrants, tablet glidants, tablet lubricants, tablet or capsule opaquants andlor tablet polishing agents.

As used herein, the term "adsorbent" is intended to mean an agent capable of holding other molecules onto its surface by physical or chemical (chemisorption) means. Such compounds include, by way of example and without li m itation, powdered and activated charcoal and other materials known to one of ordinary skill in the art.

As used herein, the term "antioxidant" is intended to mean an agent which inhibits oxidation and thus is used to prevent the deterioration of preparations by the oxidative process. Such compounds include, by way of example and without limitation, ascorbic acid, ascorbyl palmitate, butylated hydroxyanisole, butylated hydroxytoluene, hypophophorous acid, monothioglycerol, propyl gallate, sodium ascorbate, sodium bisulfite, sodium formaldehyde sulfoxylate and sodium metabisulfite and other materials known to one of ordinary skill in the art.

As used herein, the term "buffering agent" is intended to mean a compound used to resist change in pH upon dilution or addition of acid or alkali. Such compounds include, by way of example and without limitation, potassium metaphosphate, potassium phosphate, monobasic sodium acetate and sodium citrate anhydrous and dihydrate and other materials known to one of ordinary skill in the art.

As used herein, the term "sweetening agent" is intended to mean a compound used to impart sweetness to a preparation. Such compounds include, by way of example and without limitation, asp aame, dextrose, glycerin, mannitol, saccharin sodium, sorbitol and sucrose and other materials known to one of ordinary skill in the art.

As used herein, the term "tablet antiadherents" is intended to mean agents which prevent the sticking of tablet formulation ingredients to punches and dies in a tableting machine during production Such compounds include, by way of example and without limitation, magnesium stearate, talc, calcium stearate, glyceryl behenate, PEG, hydrogenated vegetable oil, mineral oil, stearic acid and other materials known to one of ordinary skill in the art.

As used herein, the term "tablet binders" is intended to mean substances used to cause adhesion of powder particles in table granulations. Such compounds include, by way of example and without limitation, acacia, alginic acid, carboxymethylcellulose sodium, poly(vinylpyrrolidone), compressible sugar (e.g., NuTab), ethylcellulose, gelatin, liquid glucose, methylcellulose, povidone and pregelatinized starch and other materials known to one of ordinary skill in the art.

When needed, binders may also be included in the tablets. Exemplary binders include acacia, tragacanth, gelatin, starch, cellulose materials such as methyl cellulose and sodium carboxy methyl cellulose, alginic acids and salts thereof, polyethylene glycol, guar gum, polysaccharide, bentonites, sugars, invert sugars, poloxamers (PLURONIC F68, PLURONIC F127), collagen, albumin, gelatin, cellulosics in nonaqueous solvents, combinations thereof and the like. Other binders include, for example, polypropylene glycol, polyoxyethylene-polypropylene copolymer, polyethylene ester, polyethylene sorbitan ester, polyethylene oxide, combinations thereof and other materials known to one of ordinary skill in the art.

As used herein, the term "tablet and capsule diluent" or "fillers" is intended to mean inert substances used as fillers to create the desired bulk, flow properties, and compression characteristics in the preparation of tablets and capsules. Such compounds include, by way of example and without limitation, dibasic calci un phosphate, kaolin, lactose, sucrose, mannitol, microcrystalline cellulose, powdered cellulose, precipitated calcium carbonate, sorbitol, and starch and other materials known to one of ordinary skill in the art.

As used herein, the term "tablet direct compression excipient" is intended to mean a compound used in direct compression tablet formulations. Such compounds include, by way of example and without limitation, dibasic calcium phosphate (e.g., Ditab) and other materials known to one of ordinary skill in the art.

As used herein, the term "tablet glidant" is intended to mean agents used in tablet and capsule formulations to reduce friction during tablet compression. Such compounds include, by way of example and without limitation, colloidal silica, cornstarch, talc, calcium silicate, magnesium silicate, colloidal silicon, silicon hydrogel and other materials known to one of ordinary skill in the art.

As used herein, the term "tablet lubricant" is intended to mean substances used in tablet formulations to reduce friction during tablet compression. Such compounds include, by way of example and without limitation, calcium stearate, magnesium stearate, mineral oil, stearic acid, and zinc stearate and other materials known to one of ordinary skill in the art.

As used herein, the term "tablet/capsule opaquant" is intended to mean a compound used to render a capsule or a tablet coating opaque. May be used alone or in combination with a colorant. Such compounds include, by way of example and without limitation, titanium dioxide and other materials known to one of ordinary skill in the art.

As used herein, the term "tablet polishing agent" is intended to mean a compound used to impart an attractive sheen to coated tablets. Such compounds include, by way of example and without limitation, carnauba wax, and white wax and other materials known to one of ordinary skill in the art.

As used herein, the term "tablet disintegrant" is intended to mean a compound used in solid dosage forms to promote the disruption of the solid mass into smaller particles which are more readily dispersed or dissolved. Exemplary disintegrants include, by way of example and without limitation, starches such as corn starch, potato starch, pre-gelatinized and modified starches thereof, sweeteners, clays, such as bentonite, microcrystalline cellulose(e.g., Avicel), carboxymethylcellulose calcium, cellulose polyacrilin potassium (e.g., Amberlite), alginates, sodium starch glycolate, gums such as agar, guar, locust bean, karaya, pectin, tragacanth and other materials known to one of ordinary skill in the art.

As used herein, the term "colorant" is intended to mean a compound used to impart color to solid (e.g., tablets) pharmaceutical preparations. Such compounds include, by way of example and without limitation, FD&C Red No. 3, FD&C Red No. 20, FD&C Yellow No. 6, FD&C Blue No. 2, D&C Green No. 5, D&C Orange No. 5, D&C Red No. 8, caramel, and ferric oxide, Ted, other F.D. & C. dyes and natural coloring agents such as grape skin extract, beet red powder, beta-carotene, annato, car mine, turmeric, paprika, and other materials known to one of ordinary skill in the art. The amount of coloring agent used will vary as desired.

As used herein, the term "flavorant" is intended to mean a compound used to impart a pleasant flavor and often odor to a pharmaceutical preparation. Exemplary flavoring agents or flavorants include synthetic flavor oils and flavoring aromatics and/or natural oils, extracts from plants, leaves, flowers, fruits and so forth and combinations thereof. These may also include cinnamon oil, oil of wintergreen, peppermint oils, clove oil, bay oil, anise oil, eucalyptus, thyme oil, cedar leave oil, oil of nutmeg, oil of sage, oil of bitter almonds and cassia oil. Other useful flavors include vanilla, citrus oil, including lemon, orange, grape, lime and grapefruit, and fruit essences, including apple, pear, peach, strawberry, raspberry, cherry, plum, pineapple, apricot and so forth. Flavors which have been found to be particularly useful include commercially available orange, grape, cherry and bubble gum flavors and mixtures thereof. The amount of flavoring may depend on a number of factors, including the organoleptic effect desired. Flavors will be present in any amount as desired by those of ordinary skill in the art. Particularly preferred flavors are the grape and cherry flavors and citrus flavors such as orange.

The present tablets can also employ one or more commonly known surface active agents or cosolvents that improve wetting or disintegration of the tablet core or layers.

Plasticizers can also be included in the tablets to modify the properties and characteristics of the polymers used in the coats or core of the tablets. As used herein, the term "plasticizer" includes all compounds capable of plasticizing or softening a polymer or binder used in invention. The plasticizer should be able to lower the melting temperature or glass transition temperature (softening point temperature) of the polymer or binder. Plasticizers, such as low molecular weight PEG, generally broaden the average molecular weight of a polymer in which they are included thereby lowering its glass transition temperature or softening point. Plasticizers also generally reduce the viscosity of a polymer. It is possible the plasticizer will impart some particularly advantageous physical properties to the osmotic device of the invention.

Plasticizers useful in the invention can include, by way of example and without limitation, low molecular weight polymers, oligomers, copolymers, oils, small organic molecules, low molecular weight polyols having aliphatic hydroxyls, ester-type plasticizers, glycol ethers, poly (propylene glycol), multi-block polymers, single block polymers, low molecular weight poly(ethylene glycol), citrate ester-type plasticizers, triacetin, propylene glycol and glycerin. Such plasticizers can also include ethylene glycol, 1,2-butylene glycol, 2,3-butylene glycol, styrene glycol, diethylene glycol, triethylene glycol, tetraethylene glycol and other poly(ethylene glycol) compounds, monopropylene glycol monoisopropyl ether, propylene glycol monoethyl ether, ethylene glycol monoethyl ether, diethylene glycol monoethyl ether, sorbitol lactate, ethyl lactate, butyl lactate, ethyl glycolate, dibutylsebacate, acetyltributylcitrate, triethyl citrate, acetyl triethyl citrate, tributyl citrate and allyl glycolate. All such plasticizers are commercially available from sources such as Aldrich or Sigma Chemical Co. It is also contemplated and within the scope of the invention, that a combination of plasticizers may be used in the present formulation. The PEG based plasticizers are available commercially or can be made by a variety of methods, such as disclosed in Poly(ethylene glycol) *Chemistry: Biotechnical and Biomedical Applications* (J. M. Harris, Ed.; Plenum Press, NY) the disclosure of which is hereby incorporated by reference.

The tablets of the invention can also include oils, for example, fixed oils, such as peanut oil, sesame oil, cottonseed oil, corn oil and olive oil; fatty acids, such as oleic acid, stearic acid and isotearic acid; and fatty acid esters, such as ethyl oleate, isopropyl myristate, fatty acid glyceridees and acetylated fatty acid glycerides. It can also be mixed with alcohols, such as ethanol, isopropanol, hexadecyl alcohol, glycerol and propylene glycol; with glycerol ketals, such as 2,2dimethyl-1,3-dioxolane-4-methanol; with ethers, such as poly(ethyleneglycol) 450, with petroleum hydrocarbons, such as mineral oil and petrolatum; with water, or with mixtures thereof; with or without the addition of a pharmaceutically suitable surfactant, suspending agent or emulsifying agent.

Soaps and synthetic detergents may be employed as surfactants and as vehicles for detergent compositions. Suitable soaps include fatty acid alkali metal, ammonium, and triethanolamine salts. Suitable detergents include cationic detergents, for example, dimethyl dialkyl ammonium halides, alkyl pyridinium halides, and alkylamine acetates; anionic detergents, for example, alkyl, aryl and olefin sulfonates, alkyl, olefin, ether and monoglyceride sulfates, and sulfosuccinates; nonionic detergents, for example, fatty amine oxides, fatty acid alkanolamides, and poly (oxyethylene)-block-poly(oxypropylene) copolymers; and amphoteric detergents, for example, alkyl β-aminopropionates and 2-alkylimidazoline quaternary ammonium salts; and mixtures thereof.

Various other components, not otherwise listed above, can be added to the present formulation for optimization of a desired active agent release profile including, by way of example and without limitation, glycerylmonostearate, nylon, cellulose acetate butyrate, d, 1-poly(lactic acid), 1,6-hexanediamine, diethylenetriamine, starches, derivatized starches, acetylated monoglycerides, gelatin coacervates, poly (styrene-maleic acid) copolymer, glycowax, castor wax, stearyl alcohol, glycerol palmitostearate, poly(ethylene), poly(vinyl acetate), poly (vinyl chloride), 1,3-butylene-glycoldimethacrylate, ethyleneglycol-dimethacrylate and methacrylate hydrogels.

It should be understood, that compounds used in the art of pharmaceutical formulation generally serve a variety of functions or purposes. Thus, if a compound named herein is mentioned only once or is used to define more than one term herein, its purpose or function should not be construed as being limited solely to that named purpose(s) or function(s).

By the term "effective amount", it is understood that, with respect to, for example, pharmaceuticals, a therapeutically effective amount is contemplated. A therapeutically effective amount is the amount or quantity of oxybutynin which is sufficient to elicit the required or desired therapeutic response, or in other words, the amount which is sufficient to elicit an appreciable biological response when administered to a patient.

For buccal, and sublingual administration, the tablets may be in the form of a caplet, chewable tablet, compressed granulate, lozenge or troche.

The first and second tablets can differ in size, shape, color and amount of oxybutynin. The tablets of the invention can assume any shape or form known in the art of pharmaceutical sciences. The device of the invention can be a pill, sphere, tablet, bar, plate, granule, agglomerate, paraboloid of revolution, ellipsoid of revolution or the like. The tablets can also include surface markings, cuttings, grooves, letters and/or numerals for the purposes of decoration, identification and/or other purposes.

The tablets of the invention can be prepared according to the methods disclosed herein or those well known in the art, more specifically according to the methods disclosed in the disclosure incorporated herein by reference. For example, according to one manufacturing technique, oxybutynin and excipients that comprise the core are mixed in solid, semi-solid or gelatinous form, then moistened and sieved through a specified screen to obtain uncoated cores. The uncoated cores are then dried in a dryer and compressed, for example, by punching.

If coated tablets are desired, the compressed and uncoated cores are then covered with a solution of suitable materials to provide the desired release profile. For example, if the tablet is to be an osmotic device, then the tablet core should be coated with a semipermeable membrane. Subsequently, the semipermeable membrane surrounding the core should be perforated with, for example, laser equipment.

The tablets of the invention can be coated with a finish coat as is commonly done in the art to provide the desired shine, color, taste or other aesthetic characteristics. Materials suitable for preparing the finish coat are well known in the art and found in the disclosures of many of the references cited and incorporated by reference herein.

The method of the invention as practiced with the system of the invention can further comprise one or more of the following steps:

(a) determining the response of the mammal to therapy with the system; and (b) adapting the system to provide the desired response in the mammal.

Step (a) can comprise the steps of determining the pharmacokinetic, pharmacodynamic, pharmacological, therapeutic, behavioral and/or toxicological response of the mammal to the system. These responses can be determined easily by those of ordinary skill in the art by monitoring the occurrence of side effects associated with the therapy, monitoring blood levels of oxybutynin, correlating blood levels of oxybutynin to particular tablet formulations or patient profile, and/or observing improvement of urinary incontinence associated symptoms.

The system of the invention can be adapted according to step (b) above as follows. For frail elderly patients, lower dosages of oxybutynin will be required. For patients which respond poorly, i.e., receive a minimal therapeutic benefit, to oxybutynin therapy, higher dosages will be required. For patients who exhibit side effects caused by oxybutynin, lower dosage will be required. For patients whose eating habits interfere with oxybutynin therapy, dosages can be adjusted according to observed plasma oxybutynin concentrations to provide the desired concentrations, i.e., undesirably low plasma oxybutynin concentrations are overcome by administering higher dosages of oxybutynin. If one particular embodiment of the system is practiced on a mammal but unwanted side-effects due to high plasma oxybutynin concentrations are observed, the system can be modified by changing the formulation(s) used.

The system of the invention is also preferably provided as a kit with which physicians and patients can easily determine the proper combination of first and second tablets that should be administered according to the above guiding principles. A start-up kit of the system is preferably used as follows. The start-up kit comprises at least two different formulations of first tablets and at least two different formulations of second tablets. The physician administers and/or prescribes one formulation from each of the first and second tablets. After a period of time, usually one to fourteen days, the patient's response is determined. Depending upon the response, the physician may administer and/or prescribe different formulations for the first and/or second tablets. Where the patient exhibits accumulation of oxybutynin, the physician may recommend lower dose first and/or second tablets, use second tablets having a shorter release profile, or use first tablets having a different release profile. Where the patient exhibits unwanted side effects during the initial part of each 24 hour period that the system is administered, the physician may recommend lower dose first tablets, second tablets having a delayed delivery of oxybutynin, or short acting controlled release first tablets. Where the patient exhibits a loss of therapeutic benefit during the latter part of each 24 hour period that the system is administered, the physician may recommend second tablets that release oxybutynin over a longer period of time or that contain a higher dose of oxybutynin.

The advantages of the present system over known systems for treating oxybutynin will include simplified modification of the dosing regimen, adaptability of the system to compensate for patient to patient variability, improved patient compliance and reduced side-effects.

The following examples should not be considered exhaustive, but merely illustrative of only a few of the many embodiments contemplated by the present invention. The methods described herein can be followed to prepare osmotic devices according to the invention.

EXAMPLE 1

Long Acting Controlled Release Tablets: 24 Hour Preparations

Long acting controlled release tablets which release oxybutynin hydrochloride over a period of about 24 hours were prepared using the following ingredients in the amounts indicated. The tablets were made in 10 and 15 mg strengths of oxybutynin.

These tablets are conventional osmotic device preparations which can be prepared according to well known procedures.

| Component × 1 Tablet | 10 mg | 15 mg |
|---|---|---|
| CORE | | |
| Oxybutynin Hydrochloride | 10.30 mg | 15.45 mg |
| Mannitol | 177.40 mg | 266.05 mg |
| Anhydrous Dextrose | 26.70 mg | 40.00 mg |
| Povidone | 16.70 mg | 25.00 mg |
| Colloidal Silicon Dioxide | 2.00 mg | 3.00 mg |
| Polyethylene Glycol 400 | 2.30 mg | 3.50 mg |
| Polyethylene Glycol 6000 | 10.00 mg | 15.00 mg |
| Tartaric Acid | 5.30 mg | 8.00 mg |
| Magnesium Stearate | 2.70 mg | 4.00 mg |
| COATING A | | |
| Cellulose 101[(1)] | 5.32 mg | 9.38 mg |
| Cellulose 102[(2)] | 10.64 mg | 18.74 mg |
| Polyethylene Glycol 400 | 0.84 mg | 1.48 mg |
| COATING B | | |
| Hydroxypropyl methylcellulose 2910 | 5.92 mg | 7.40 mg |
| Copolyvidone | 4.80 mg | 6.00 mg |
| Polyethylene Glycol 6000 | 1.68 mg | 2.10 mg |
| Titanium Dioxide | 3.60 mg | 4.50 mg |

[(1)]: Acetyl content of 32.0% by weight of CA. Viscosity of 210.0 cP (ASTM method D-1343). Average Molecular weight 40,000.
[(2)]: Acetyl content of 39.8% by weight of CA. Viscosity of 38.0 cP (ASTM method D-1343). Average Molecular weight 38,000.

A controlled release tablet according to this example would generally provide a release of oxybutynin according to the following exemplary table.

| Sampling Time | Dissolved % | |
|---|---|---|
| (hours) | 10 mg | 15 mg |
| 3 | 13–33 | 10–25 |
| 7 | 40–58 | 30–50 |
| 11 | 56–72 | 45–65 |
| 15 | 65–80 | 55–75 |
| 23 | Min. 70 | >70 |

An exemplary method for the preparation of these tablets follows. Pilot scale batches of oxybutynin HCl 10 mg, and 15 mg, strength tablets were prepared by mixing 61.80 g of oxybutynin HCl, 1064.40 g of mannitol, 160,20 g of anhydrous dextrose, 31.80 g of tartaric acid and 50.2 g or povidone. The mixture was moistened with a blend of 180.00 ml of alcohol (96°), 50.00 g of povidone, 60.00 g of poly(ethylene glycol), 6000 and 13.80 g of poly(ethylene glycol) 400. The blend was granulated and dried at 40–50° C. for 2 hours. Then, it was screened and mixed with 12.00 g of colloidal silicon dioxide. The blend was mixed to homogeneity and 16.20 g of magnesium stearate was added as lubricant. The final blend was tabletted using biconcave 8.0-mm (or 9.0-mm for the 15 mg) diameter punches. The average weight of the cores was about 253.4 mg (380.0 mg for the 15 mg tablets) hardness of about 5 to 12 kp.

A composition to cover the cores was prepared as follows: a polymer suspension was prepared dissolving 47.88 g (75.04 g) of cellulose 101, 95.76 g (149.92 g) of cellulose 102 and 7.56 g (11.84) of poly(ethylene glycol) 400 in a mixture of methylene chloride-methyl alcohol (70:30 v/v). This polymer mixture was sprayed onto the tablets in a conventional pan coater to obtain film-coated tablets which membrane coating weighed an average of about 18 mg (30 mg for the 15 mg strength tablets). A 0.50-mm hole was drilled through the coating in one face of the tablet. The final coating was prepared by mixing 53.28 g of hydroxypropyl methylcellulose 2910, 43.20 g of copolyvidone, 15.12 g poly(ethylene glycol) 6000 and 32.40 g of titanium dioxide in a mixture of methylene chloride-alcohol 96° (70:30 v/v). This polymer mixture was sprayed onto the tablets in a conventional pan coater to obtain film-coated tablets having a membrane weighing about 16 mg (20 mg for the 15 mg strength tablets) approximately.

EXAMPLE 2

Long Acting Controlled Release Tablets: 24 Hour Preparations With (S)-Oxybutynin Long acting controlled release tablets which release S-oxybutynin over a period of about 24 hours were prepared using the following ingredients in the amounts indicated. The tablets were made in 300 mg strength of S-oxybutynin hydrochloride. These tablets are conventional osmotic device preparations which can be prepared according to well known procedures. The amount of S-oxybutynin hydrochloride, and other ingredients, in the tables can be varied as needed.

| Component × 1 Tablet | 300 mg |
|---|---|
| CORE | |
| S-Oxybutynin Hydrochloride | 300.000 mg |
| Microcrystalline Cellulose | 219.500 mg |
| Mannitol | 182.000 mg |
| Anhydrous Dextrose | 40.000 mg |
| Copolyvidone | 12.000 mg |
| Polyethylene Glycol 6000 | 10.000 mg |
| Polyethylene Glycol 400 | 2.500 mg |
| Tartaric Acid | 7.000 mg |
| Colloidal Silicon Dioxide | 12.000 mg |
| Magnesium Stearate | 15.000 mg |
| COATING A1 | |
| Copolyvidone | 32.000 mg |
| Talc | 32.000 mg |
| COATING A2 | |
| Cellulose 101 | 30.900 mg |
| Cellulose 102 | 16.600 mg |
| Polyethylene Glycol 400 | 2.500 mg |
| COATING B | |
| Hydroxypropylmethylcellulose 2910 | 12.055 mg |
| Polyethylene Glycol 6000 | 3.436 mg |
| Titanium Dioxide | 4.359 mg |
| Red Ferric Oxide | 0.150 mg |

A modified version of the method of Example 1 was used to prepare these tablets.

EXAMPLE 3

Long Acting Controlled Release Tablets: 3–24 hr Release

This system maintains therapeutically effective levels of S-oxybutynin in a mammal for a period beginning about 3.5 hours after administration and ending about 24 hours after administration. This exemplary tablet releases S-oxybutynin for a period beginning about 3 hours after administration and ending about 23–24 hours after administration. The tablets are made in a 300 mg strength of S-oxybutynin hydrochloride.

| Component × 1 Tablet | 300 mg |
|---|---|
| CORE | |
| S-Oxybutynin Hydrochloride | 300.000 mg |
| Microcrystalline Cellulose | 219.500 mg |
| Mannitol | 182.000 mg |
| Anhydrous Dextrose | 40.000 mg |
| Copolyvidone | 12.000 mg |
| Polyethylene Glycol 6000 | 10.000 mg |
| Polyethylene Glycol 400 | 2.500 mg |
| Tartaric Acid | 7.000 mg |
| Colloidal Silicon Dioxide | 12.000 mg |
| Magnesium Stearate | 15.000 mg |
| COATING A1 | |
| Copolyvidone | 32.000 mg |
| Talc | 32.000 mg |
| COATING A2 | |
| Cellulose 101 | 30.900 mg |
| Cellulose 102 | 16.600 mg |
| Polyethylene Glycol 400 | 2.500 mg |
| COATING B | |
| Methacrylic Acid copolymer, USP Type A | 21.800 mg |
| Polyethylene Glycol 6000 | 1.450 mg |
| Talc | 7.000 mg |
| Titanium Dioxide | 4.600 mg |
| Red Ferric Oxide | 0.150 mg |

These tablets were made according to a modified version of the procedure of Example 1.

EXAMPLE 4

Long Acting Controlled Release Tablets: 1–12 hr Release

This system maintains therapeutically effective levels of racemic oxybutynin in a mammal for a period beginning about 1 hour after administration and ending about 12 hours after administration. This exemplary tablet releases racemic oxybutynin for a period beginning about 0.1 hour after administration and ending about 12 hours after administration. The tablets are made in 10 and 15 mg strengths of racemic oxybutynin hydrochloride.

| Component × 1 Tablet | 10 mg | 15 mg |
|---|---|---|
| CORE | | |
| Oxybutynin Hydrochloride | 10.30 mg | 15.45 mg |
| Mannitol | 177.40 mg | 266.05 mg |
| Anhydrous Dextrose | 26.70 mg | 40.00 mg |
| Povidone | 16.70 mg | 25.00 mg |
| Colloidal Silicon Dioxide | 2.00 mg | 3.00 mg |
| Polyethylene Glycol 400 | 2.30 mg | 3.50 mg |
| Polyethylene Glycol 6000 | 10.00 mg | 15.00 mg |
| Tartaric Acid | 5.30 mg | 8.00 mg |
| Magnesium Stearate | 2.70 mg | 4.00 mg |
| COATING A | | |
| Cellulose 101 | 10.64 mg | 18.75 mg |
| Cellulose 102 | 5.32 mg | 9.37 mg |
| Polyethylene Glycol 400 | 0.84 mg | 1.48 mg |
| COATING B | | |
| Hydroxypropylmethylcellulose 2910 | 5.92 mg | 7.40 mg |
| Copolyvidone | 4.80 mg | 6.00 mg |
| Polyethylene Glycol 6000 | 1.68 mg | 2.10 mg |
| Titanium Dioxide | 3.60 mg | 4.50 mg |

These tablets were made according to a modified version of the procedure of Example 1.

EXAMPLE 5

Long Acting Controlled Release Tablets: 1–12 hr Release S-Oxybutynin

This system maintains therapeutically effective levels of S-oxybutynin in a mammal for a period beginning about 1 hour after administration and ending about 12 hours after administration. This exemplary tablet releases S-oxybutynin for a period beginning about 0.1 hour after administration and ending about 12 hours after administration. The tablets are made in a 300 mg strength of S-oxybutynin hydrochloride.

| Component × 1 Tablet | 300 mg |
|---|---|
| CORE | |
| S-Oxybutynin Hydrochloride | 300.00 mg |
| Microcrystalline Cellulose | 219.50 mg |
| Mannitol | 182.00 mg |
| Anhydrous Dextrose | 40.00 mg |
| Copolyvidone | 12.00 mg |
| Polyethylene Glycol 6000 | 10.00 mg |
| Polyethylene Glycol 400 | 2.50 mg |
| Tartaric Acid | 7.00 mg |
| Colloidal Silicon Dioxide | 12.00 mg |
| Magnesium Stearate | 15.00 mg |
| COATING A1 | |
| Copolyvidone | 32.00 mg |
| Talc | 32.00 mg |
| COATING A2 | |
| Cellulose 101 | 39.20 mg |
| Cellulose 102 | 8.30 mg |
| Polyethylene Glycol 400 | 2.50 mg |
| COATING B | |
| Hydroxypropyl methylcellulose 2910 | 12.055 mg |
| Polyethylene Glycol 6000 | 3.436 mg |
| Titanium Dioxide | 4.359 mg |
| Red Ferric Oxide | 0.150 mg |

These tablets were made according to a modified version of the procedure of Example 1.

EXAMPLE 6

Long Acting Delayed and Controlled Release Tablets: 12–24 hr Release

This system maintains therapeutically effective levels of racemic oxybutynin in a mammal for a period beginning about 12 hour after administration and ending about 24 hours after administration. This exemplary tablet releases racemic oxybutynin for a period beginning about 11–12 hours after administration and ending about 23–24 hours after administration. The tablets are made in 10 and 15 mg strengths of racemic oxybutynin hydrochloride.

| Component × 1 Tablet | 10 mg | 15 mg |
|---|---|---|
| CORE | | |
| Oxybutynin Hydrochloride | 10.30 mg | 15.45 mg |
| Mannitol | 177.40 mg | 266.05 mg |
| Anhydrous Dextrose | 26.70 mg | 40.00 mg |
| Povidone | 16.70 mg | 25.00 mg |
| Colloidal Silicon Dioxide | 2.00 mg | 3.00 mg |
| Polyethylene Glycol 400 | 2.30 mg | 3.50 mg |
| Polyethylene Glycol 6000 | 10.00 mg | 15.00 mg |
| Tartaric Acid | 5.30 mg | 8.00 mg |
| Magnesium Stearate | 2.70 mg | 4.00 mg |
| COATING A | | |
| Cellulose 101 | 10.64 mg | 18.75 mg |
| Cellulose 102 | 5.32 mg | 9.37 mg |
| Polyethylene Glycol 400 | 0.84 mg | 1.48 mg |
| COATING B | | |
| Methacrylic Acid copolymer, USP Type B | 5.92 mg | 7.40 mg |
| Polyethylene Glycol 6000 | 0.54 mg | 0.67 mg |
| Talc | 2.40 mg | 3.00 mg |
| Titanium Dioxide | 1.56 mg | 1.95 mg |

These tablets were made according to a modified version of the procedure of Example 1.

EXAMPLE 7

Long Acting Delayed and Controlled Release Tablets: 12–24 hr Release S-Oxybutynin This system maintains therapeutically effective levels of S-oxybutynin in a mammal for a period beginning about 12 hour after administration and ending about 24 hours after administration. This exemplary tablet releases S-oxybutynin for a period beginning about 11–12 hours after administration and ending about 23–24 hours after administration. The tablets are made in a 300 mg strength of S-oxybutynin hydrochloride.

| Component × 1 Tablet | 300 mg |
|---|---|
| CORE | |
| S-Oxybutynin Hydrochloride | 300.00 mg |
| Microcrystalline Cellulose | 219.50 mg |
| Mannitol | 182.00 mg |
| Anhydrous Dextrose | 40.00 mg |
| Copolyvidone | 12.00 mg |
| Polyethylene Glycol 6000 | 10.00 mg |
| Polyethylene Glycol 400 | 2.50 mg |
| Tartaric Acid | 7.00 mg |
| Colloidal Silicon Dioxide | 12.00 mg |
| Magnesium Stearate | 15.00 mg |
| COATING A1 | |
| Copolyvidone | 32.00 mg |
| Talc | 32.00 mg |
| COATING A2 | |
| Cellulose 101 | 39.20 mg |

| Component × 1 Tablet | 300 mg |
|---|---|
| Cellulose 102 | 8.30 mg |
| Polyethylene Glycol 400 | 2.50 mg |
| COATING B | |
| Methacrylic Acid copolymer, USP Type B | 21.80 mg |
| Polyethylene Glycol 6000 | 1.45 mg |
| Talc | 7.00 mg |
| Titanium Dioxide | 4.60 mg |
| Red Ferric Oxide | 0.150 mg |

These tablets were made according to a modified version of the procedure of Example 1.

EXAMPLE 8

Rapid Release Tablets

These tablets release about 80% of their oxybutynin charge rapidly within about 0.5 hours after administration. These tablets maintain therapeutically effective levels of oxybutynin in a mammal for a period of up to about 3 hours after administration. This exemplary tablet releases oxybutynin for a period of up to about 0.5–3.0 hours after administration. The tablets are made in a 5 mg strength of oxybutynin hydrochloride.

| Component × 1 Tablet | 5 mg |
|---|---|
| CORE | |
| Oxybutynin Hydrochloride | 5.15 mg |
| Monohydrate Lactose | 121.00 mg |
| Microcrystalline Cellulose | 36.50 mg |
| Povidone | 5.40 mg |
| Colloidal Silicon Dioxide | 1.20 mg |
| Aluminium Lake Brilliant Blue | 0.15 mg |
| Croscarmellose Sodium | 3.60 mg |
| Magnesium Stearate | 1.50 mg |
| Sodium Lauryl Sulfate | 3.50 mg |

These tablets are very similar to commercially available Ditropan™ tablets sold by Laboratorios Phoenix (Argentina).

EXAMPLE 9

Short Acting Controlled Release Tablets

A pilot scale batch of oxybutynin HCl (10 mg strength) short-acting controlled release tablets is prepared according to the same manufacturing procedure described for the cores of the EXAMPLE 1 except that the coating formulation is modified as follows: a polymer suspension is prepared by dissolving 97.20 g of cellulose 101, 39.06 g of cellulose 102 and 7.74 g of poly(ethylene glycol) 400 in a mixture of methylene chloride-methyl alcohol (70:30 v/v). This polymer mixture is sprayed onto the tablets in a conventional pan coater to obtain film-coated tablets which membrane weighed an average of about 16 mg. A 0.50-mm hole is drilled through the coating in one face of the tablet. The final coating is prepared by mixing 5328 g of hydroxypropyl methylcellulose 2910, 43.20 g of copolyvidone, 15.12 g poly(ethylene glycol) 6000 and 32.40 g of titanium dioxide in a mixture of methylene chloride-alcohol (96 0, 70:30 v/v). This polymer mixture is sprayed onto the tablets in a conventional pan coater to obtain film-coated tablets which membrane weighed an average of about 12 mg.

EXAMPLE 10

Immediate Release Tablets

The tablets of this example are made as follows. The tables include exemplary formulations for the different individual types of tablets.

(a) Effervescent Tablets

| Component × 1 Tablet | 5 mg strength |
|---|---|
| Oxybutynin Hydrochloride | 5.15 mg |
| Sorbitol | 417.93 mg |
| Citric Acid | 240.00 mg |
| Sodium Bicarbonate | 115.00 mg |
| Polyethylene Glycol 6000 | 18.00 mg |
| Orange flavor | 3.48 mg |
| Saccharin Sodium | 0.44 mg |
| Total | 800.00 mg |

A pilot scale batch of oxybutynin HCl (5 mg) effervescent tablets is prepared by mixing 5.15 g of oxybutynin HCl, 417.93 g of sorbitol, 240,00 g of citric acid, 115.00 g of sodium bicarbonate (dried during 2 hours at 105° C.), 18.00 g of poly(ethylene glycol) 6000, 3.48 g of orange flavor and 0.44 g of saccharin sodium. The blend is mixed and screened and the final blend was tabletted at a maximum 25% relative atmospheric humidity, using biplanar 14.0-mm diameter punches. Cores should preferably weigh an average of about 800.0 mg having a hardness of about 10 to 14 kp.

(b) Chewable Tablets

| Component × 1 Tablet | 5 mg strength |
|---|---|
| Oxybutynin Hydrochloride | 5.15 mg |
| Microcrystalline Cellulose | 276.31 mg |
| Sorbitol | 140.00 mg |
| Dextrose | 54.50 mg |
| Poly(ethylene glycol) 6000 | 12.00 mg |
| Colloidal Silicon Dioxide | 1.50 mg |
| Magnesium Stearate | 4.20 mg |
| Strawberry flavor | 5.80 mg |
| Saccharin Sodium | 0.54 mg |
| Total | 500.00 mg |

A pilot scale batch of oxybutynin HCI (5 mg) chewable tablets is prepared by mixing 5.15 g of oxybutynin HCI, 140.00 g of sorbitol, 276.31 g of microcrystalline cellulose, 54.50 g of dextrose, 12.00 g of poly(ethylene glycol) 6000, 5.80 g of strawberry flavor and 0.54 g of saccharin sodium. The blend is mixed and screened, and the final blend is mixed with 1.50 g of colloidal silicon dioxide. 4.20 g of magnesium stearate was added as lubricant. The blend is tabletted using biplanar 10.0-mm diameter punches. Cores preferably weighed an average of about 500.0 mg having a hardness of about 12 to 15 kp.

(c) Very Rapidly Dissolving Tablets

| Component × 1 Tablet | 5 mg strength |
|---|---|
| Oxybutynin Hydrochloride | 5.15 mg |
| Microcrystalline Cellulose | 15.00 mg |
| Sorbitol | 15.40 mg |
| Crospovidone | 13.55 mg |
| Magnesium Stearate | 0.25 mg |
| Orange flavor | 0.60 mg |
| Saccharin Sodium | 0.05 mg |
| Total | 50.00 mg |

A pilot scale batch of oxybutynin HCl (5 mg) very rapidly dissolving tablets is prepared by mixing 5.15 g of oxybutynin HCl, 15.40 g of sorbitol, 15.00 g of microcrystalline cellulose, 13.55 g of crospovidone, 0.60 g of orange flavor and 0.05 g of saccharin sodium. The blend is mixed and screened, and the final blend is mixed with 0.25 g of magnesium stearate. The blend is tabletted using biconcave 5.0-mm diameter punches. Cores preferably weigh an average of about 50.0 mg having a hardness of about 4 to 7 kp.

The above is a detailed description of particular embodiments of the invention. It is recognized that departures from the disclosed embodiment may be made within the scope of the invention and that obvious modifications will occur to a person skilled in the art. The full scope of the invention is set out in the claims that follow and their equivalents. Accordingly, the claims and specification should not be construed to unduly narrow the full scope of protection to which the invention is entitled.

Those of skill in the art should, in light of the present disclosure, appreciate that many changes can be made in the specific embodiments where are disclosed herein and still obtain a like or similar result without departing from the spirit and scope of the invention. All of the compositions and methods disclosed and claimed herein can be made and executed without undue experimentation in light of the present disclosure. It will be apparent that certain compounds which are both physiologically and chemically related may be substituted for the therapeutic compound described herein while the same or similar results are achieved.

I claim:

1. A two-tablet system for treating urinary incontinence in a mammal, the system comprising:

a first tablet comprising a first oxybutynin charge which is released after at least about one second up to less than about twelve hours after administration of the first tablet; and a second tablet comprising a second oxybutnin charge which is released after at least about three hours up to less than about thirty hours after administration of the second tablet, wherein the first and second tablet together provide a sustained delivery of oxybutynin for a total period of about 18–30 hours, the system maintains therapeutic levels of oxybutynin for a period of about 18 to 24 hours, and the first and second tablets are administered on a once daily basis;

wherein each tablet exhibits a different profile and the system provides reduced side effects as compared to a conventional system providing the same therapeutic dose.

2. The system of claim 1, wherein the first and second tablets maintain a therapeutic level of oxybutynin in the plasma of the mammal for a period of at least about 22 hours.

3. The system of claim 1, wherein the first tablet is a rapid release or short acting controlled release dosage form and the second tablet is a longer acting controlled release dosage form.

4. The system of claim 1, wherein the first tablet releases all of its oxybutynin charge within about six hours after administration of the first tablet, and the second tablet begins to release its oxybutynin charge within about five hours after administration of the first tablet and completes its release of oxybutynin within about 24 hours after administration of the first tablet.

5. The system of claim 1, wherein the first tablet releases all of its oxybutynin charge less than two hours after administration of the first tablet, and the second tablet begins to release its oxybutynin charge within about four hours after administration of the first tablet and completes its release of oxybutynin within about 23 hours after administration of the first tablet.

6. The system of claim 1, wherein the second tablet begins to release its oxybutynin after the first tablet has released at least a majority of its oxybutynin.

7. The system of claim 1, wherein the first tablet begins to release its oxybutynin after at least one second after administration of the first tablet and the second tablet begins to release its oxybutynin after at least about two hours after administration of the second tablet.

8. The system of claim 1, wherein the first tablet releases its oxybutynin in the upper GI tract and the second tablet releases its oxybutynin in the lower GI tract.

9. The system of claim 1, wherein the first tablet is a gastric release tablet and the second tablet is an enteric or colonic release tablet.

10. The system of claim 1, wherein the first tablet releases its oxybutynin in at least one of the buccal cavity, esophagus, stomach, duodenum, jejunum and upper small intestine, and the second tablet releases its oxybutynin farther down the GI tract.

11. The system of claim 1, wherein the first and second tablets are independently one of a pressed tablet, layered tablet, osmotic device tablet, coated tablet, uncoated tablet, enteric coated tablet, multiple compressed tablets, centered tablets, prolonged release tablet, slow release tablet, buccal tablet, sublingual tablet and molded tablet.

12. The system of claim 1, wherein the system maintains a plasma oxybutynin concentration between about 0.5 to about 10 ng/ml in the mammal for at least half of a twenty four hour period following administration of the first tablet.

13. The system of claim 1, wherein the system maintains a plasma oxybutynin concentration between about 1 to about 8 ng/ml in the mammal for at least half of a twenty four hour period following administration of the first tablet.

14. The system of claim 1, wherein the first charge of oxybutynin is about 0.01 mg to about 5.0 mg and the second charge of oxybutynin is about 5 mg to about 15 mg of oxybutynin.

15. The system of claim 14, wherein the first tablet provides therapeutic levels of oxybutynin for a period of less than about 6 hours after administration of the first tablet, and the second tablet provides therapeutic levels of oxybutynin for a period beginning no sooner than about 3 hours and ending about 24 hours after administration of the first tablet.

16. The system of claim 1, wherein the second tablet provides a delayed and controlled release of oxybutynin.

17. The system of claim 1, wherein neither tablet alone maintains therapeutic levels of oxybutynin for a 24 hour period.

18. The system of claim 1, wherein the first and second tablets together provide a sustained delivery of oxybutynin for a total period of about 18–24 hours and the system maintains therapeutic levels of oxybutynin for a period of about 24 hours.

19. A method of treating urinary incontinence in a mammal with oxybutynin, the method comprising the steps of:
administering on a daily basis a first tablet comprising a first charge of oxybutynin and having a first release profile for the release of oxybutynin; and
administering on a daily basis a second tablet comprising a second charge of oxybutynin and having a second release profile for the release of oxybutynin;
wherein the first and second tablets have different release profiles for the release of oxybutynin; the first and second tablets together but not individually maintain therapeutic plasma levels of oxybutynin for a period of about 18–24 hours; and the system provides reduced effects as compared to a conventional system providing the same therapeutic dose.

20. The method of claim 19, wherein the first and second tablets are administered concurrently, and the second tablet begins to release its oxybutynin charge after the first tablet has completed releasing at least a majority of its oxybutynin charge.

21. The method of claim 19, wherein the first and second tablets are administered sequentially, the first tablet begins to release its oxybutynin after at least one second after administration of the first tablet, the second tablet is administered at least about two hours after administration of the first tablet and the second tablet begins to release its oxybutynin after at least about two hours after administration of the second tablet.

22. The method of claim 19, wherein the first tablet releases its oxybutynin charge in the upper GI tract and the second tablet releases its oxybutynin charge in the lower GI tract.

23. The method of claim 19, wherein the first tablet is a gastric release tablet and the second tablet is at least one of an enteric and colonic release tablet.

24. The method of claim 19, further comprising the steps of:
determining the response of the mammal to therapy with the system; and
adapting the system to provide the desired response in the mammal.

25. The method of claim 24, wherein the adapting step comprises at least one of (1) employing a different formulation for at least the first or second tablet; and (2) changing the timing of administration of the first and second tablets.

26. The method of claim 24, wherein the determining step comprises determining at least one of the pharmacokinetic, pharmacodynamic, pharmacological, therapeutic, behavioral and toxicological response of the mammal to the system.

27. The method of claim 19, wherein the first and second tablets are administered concurrently, the first tablet begins to release its oxybutynin charge within one hour after administration and the second tablet begins to release its oxybutynin charge at least about three hours after administration.

28. The method of claim 27, wherein the first tablet completes its delivery of oxybutynin within about six hours after administration and the second tablet completes its delivery of oxybutynin within about twenty-four hours after administration.

29. The method of claim 27, wherein the second tablet begins to release its oxybutynin at most about twelve hours after administration.

30. The method of claim 19, wherein the first and second tablets are administered concurrently; both tablets begin to release their respective oxybutynin charges within about one hour after administration; the first tablet completes its delivery of oxybutynin within about six hours after administration; and the second tablet completes its delivery of oxybutynin within about twenty-four hours after administration.

31. The method of claim 30, wherein the second tablet completes its delivery of oxybutynin within about twenty-two hours after administration.

* * * * *